United States Patent [19]

Häbich et al.

[11] Patent Number: 5,633,231
[45] Date of Patent: May 27, 1997

[54] VALINE-CONTAINING PSEUDOPEPTIDES WITH ANTIVIRAL ACTIVITY

[75] Inventors: Dieter Häbich, Wuppertal; Thomas J. Schulze, Köln; Jürgen Reefschläger; Jutta Hansen, both of Wuppertal; Rainer Neumann, Köln; Gert Streissle, Wuppertal; Arnold Paessens, Haan, all of Germany

[73] Assignee: Bayer Aktiengesellschaft, Leverkusen, Germany

[21] Appl. No.: 301,506

[22] Filed: Sep. 7, 1994

[30] Foreign Application Priority Data

Sep. 14, 1993 [DE] Germany .................... 43 31 135.0

[51] Int. Cl.$^6$ ................ C07D 241/04; C07D 211/06
[52] U.S. Cl. ................ 514/18; 514/19; 514/20; 544/353; 544/224; 544/335; 530/331; 546/335; 546/336; 546/175; 546/146; 546/147; 548/568; 549/53; 549/407
[58] Field of Search ................ 544/406, 355; 546/168, 301, 340, 290, 156, 341; 548/493, 255; 530/331; 514/311, 419, 259, 255, 351, 249, 357, 20, 18, 19; 564/153, 237

[56] References Cited

U.S. PATENT DOCUMENTS 5,086,069  2/1992  Klein et al. .................... 514/399
5,492,896  2/1996  Häbich et al. .................... 514/18

FOREIGN PATENT DOCUMENTS 0611776  8/1994  European Pat. Off. .

OTHER PUBLICATIONS

Chemical Abstracts, P.E. Reed et al, vol. 114, No. 17, Apr. 29, 1991 Abstract No. 164760W.
Chemical Abstracts, M. Raju et al., vol. 115, No. 9, Sep. 2, 1991 Abstract No. 92899u.
Galpin et al., "Analogs of chymostatin", Chemical Abstracts 100:19,717u, 1984.
Galpin et al., "Synthetic peptides", Chemical Abstracts 101:23,948h, 1984.
Galpin et al., "Synthetic analogs of the proteinase inhibitor: chymostatin," Chemical Abstracts 101:192,438x, 1984.

Primary Examiner—Matthew V. Grumbling
Attorney, Agent, or Firm—Sprung Horn Kramer & Woods

[57] ABSTRACT

The present invention relates to valine-containing, substituted pseudopeptides of the general formula (I)

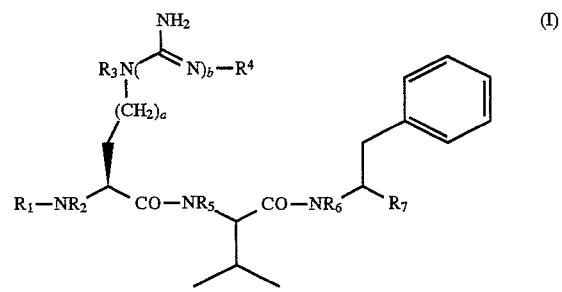

in which
the substituents have the meaning given in the description, to processes for their preparation, and to their use as anti-viral agents, in particular against cytomegaloviruses.

8 Claims, No Drawings

VALINE-CONTAINING PSEUDOPEPTIDES WITH ANTIVIRAL ACTIVITY

The present invention relates to novel valine-containing pseudopeptides with antiviral activity, to processes for their preparation, and to their use as antiviral agents, in particular against cytomegaloviruses.

In the publications J. Antibiot. 44, 1019 (1991) and FEBS Letters 3, 253 (1993) and in Patent Application WO 92/22570, peptide aldehydes are described which are inhibitors of the HIV protease and of picornavirus proteases. Furthermore, peptide aldehydes have been described which are inhibitors of serine proteases [U.S. Pat. No. 5,153,176; EP 526 877].

Various nucleoside and nucleotide analogues, anthraquinone derivatives, cobalt complexes, macrolides and acylpeptides [EP 488 041] are classes of compounds which are known to have anti-cytomegalovirus activity.

The present invention now relates to novel valine-containing substituted pseudopeptides which possess antiviral activity and are of the general formula (I)

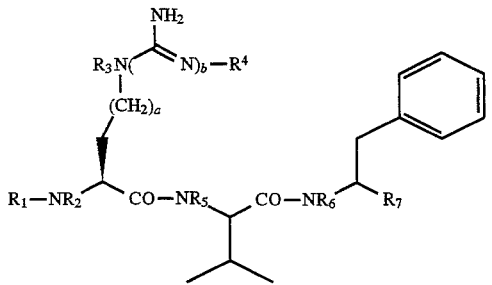

in which a represents a number 2 or 3, b represents a number 0 or 1, $R^1$ represents hydrogen, or represents an amino protective group, or represents a radical of the formula $R^8$—$NR^9$—CO—, $R^{10}$—$(CH_2)_c$—CO—, $R^{11}$—$(CH_2)_d$—O—CO, or represents a radical of the formula —$SO_2$—$R^{12}$, in which $R^8$ denotes cycloalkyl having 3 to 6 carbon atoms, or straight-chain or branched alkyl having up to 18 carbon atoms which is optionally substituted by hydroxyl, straight-chain or branched alkoxy having up to 4 carbon atoms, halogen, trifluoromethyl, trifluoromethoxy or cycloalkyl having 3 to 6 carbon atoms, or by aryl having 6 to 10 carbon atoms which, for its part, can be substituted identically or differently up to two times by carboxyl, cyano, hydroxyl, halogen, perhalogenoalkyl having up to 5 carbon atoms, or by straight-chain or branched acyl, alkoxy or alkoxycarbonyl having in each case up to 6 carbon atoms, or alkyl is optionally substituted by a group of the formula —$CO_2R^{13}$ in which $R^{13}$ denotes hydrogen, or straight-chain or branched alkyl or alkenyl having in each case up to 8 carbon atoms which are optionally substituted by phenyl, or $R^8$ denotes aryl having 6 to 10 carbon atoms which is optionally substituted identically or differently up to three times by carboxyl, amino, halogen, hydroxyl, cyano, perhalogenoalkyl having up to 5 carbon atoms or by straight-chain or branched acyl, alkoxy, vinylalkoxycarbonyl, alkoxycarbonyl or having in each case up to 6 carbon atoms, which, for its part, is substituted by straight-chain or branched alkoxy having up to 6 carbon atoms, or denotes an amino acid radical of the formula,

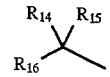

in which $R^{14}$ and $R^{15}$ are identical or different and denote hydrogen or methyl, or $R^{14}$ and $R^{15}$ together form a 5- or 6-membered saturated carbocyclic ring, or $R^{14}$ denotes hydrogen or methyl, and $R^{15}$ denotes cycloalkyl having 3 to 8 carbon atoms or aryl having 6 to 10 carbon atoms, or hydrogen, or denotes straight-chain or branched alkyl having up to 8 carbon atoms, where the alkyl is optionally substituted by methylthio, hydroxyl, mercapto or guanidyl, or by a group of the formula —$NR^{17}R^{18}$ or $R^{19}$—OC—, in which $R^{17}$ and $R^{18}$, independently of each other, denote hydrogen, straight-chain or branched alkyl having up to 8 carbon atoms, or phenyl, and $R^{19}$ denotes hydroxyl, benzyloxy, alkoxy having up to 6 carbon atoms, or the above-listed group —$NR^{17}R^{18}$, $R^{16}$ denotes straight-chain or branched alkyl having up to 8 carbon atoms which is optionally substituted by hydroxyl or straight-chain or branched alkoxy having up to 6 carbon atoms, or denotes carboxyl, allyloxycarbonyl, straight-chain or branched alkoxycarbonyl having up to 8 carbon atoms, or benzyloxycarbonyl, or the alkyl is optionally substituted by cycloalkyl having 3 to 8 carbon atoms or by aryl having 6 to 10 carbon atoms which, for its part, is substituted by hydroxyl, halogen, nitro, alkoxy having up to 8 carbon atoms, or by the group —$NR^{17}R^{18}$, in which $R^{17}$ and $R^{18}$ have the abovementioned meanings, or the alkyl is optionally substituted by a 5- to 6-membered nitrogen-containing heterocycle or indolyl in which the corresponding —NH-functions are optionally protected by alkyl having up to 6 carbon atoms or by an amino protective group, or $R^8$ denotes a radical of the formula,

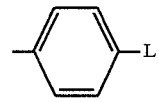

in which

L denotes phenyl or pyridyl, $R^9$ denotes hydrogen, straight-chain or branched alkyl having up to 6 carbon atoms, or an amino protective group, $R^{10}$ denotes straight-chain or branched alkyl having up to 8 carbon atoms, or denotes aryloxy or aryl having in each case 6 to 10 carbon atoms, indolyl, quinolyl, quinoxalinyl, isoquinolyl or a 5- to 7-membered, saturated or unsaturated heterocycle having up to 3 heteroatoms from the group comprising S, N or O, where the cycles can be substituted identically or differently up to 3 times by carboxyl, cyano, hydroxyl, halogen, amino, nitro, methylamino, perhalo-genoalkyl having up to 5 carbon atoms or by straight-chain or branched alkyl, acyl, alkoxy or alkoxycarbonyl having in each case up to 6 carbon atoms, or aryl is also optionally substituted by a 5- to 7-membered, saturated or unsaturated heterocycle having up to 3 heteroatoms from the group comprising S, N or O, which, for its part, can be substituted by phenyl, or $R^{10}$ denotes a radical of the formula

[chemical structures]

in which

L' has the abovementioned meaning of L and is identical to or different from the latter, $R^{20}$ denotes phenyl or naphthyl, c denotes a number 0, 1, 2 or 3, d denotes a number 0, 1, 2 or 3, $R^{11}$ has the abovementioned meaning of $R^{10}$ and is identical to or different from the latter, $R^{12}$ denotes methyl, phenyl or naphthyl which is optionally substituted identically or differently up to 4 times by methyl or methoxy, or denotes a radical of the formula

[chemical structure]

$R^2$, $R^3$, $R^5$ and $R^6$ are identical or different and represent hydrogen, straight-chain or branched alkyl having up to 4 carbon atoms, or represent an amino protective group, $R^4$ represents hydrogen, nitro, an amino protective group, or a radical of the formula —$SO_2R^{21}$, in which $R^{21}$ has the abovementioned meaning of $R^{12}$ and is identical to or different from the latter, $R^7$ represents formyl or carboxyl, or represents straight-chain or branched alkoxycarbonyl having up to 8 carbon atoms, or represents a radical of the formula —$CH_2$—$OR^{22}$ or —$CH(OR^{23})_2$, in which $R^{22}$ and $R^{23}$ are identical or different and denote hydrogen, straight-chain or branched alkyl having up to 6 carbon atoms, or a hydroxyl protective group, and salts thereof, with the proviso that if a represents the number 2, b represents the number 1 and $R^5$ represents hydrogen, $R^1$ may not denote the radical of the formula $R^8$—NH—CO—.

The compounds of the general formula (I) according to the invention may also be present in the form of their salts. Salts with organic and inorganic bases or acids may be mentioned here in a general manner.

Acids which can be added on preferably include hydrohalic acids, such as, for example, hydrofluoric acid, hydrochloric acid and hydrobromic acid, in particular hydrofluoric and hydrochloric acids, and, additionally, phosphoric acid, nitric acid, sulphuric acid, monofunctional and bifunctional carboxylic acids and hydroxycarboxylic acids, such as, for example, acetic acid, maleic acid, malonic acid, oxalic acid, gluconic acid, succinic acid, fumaric acid, tartaric acid, citric acid, salicylic acid, sorbic acid and lactic acid, as well as sulphonic acids, such as, for example, p-toluenesulphonic acid, 1,5-naphthalenedisulphonic acid or camphorsulphonic acid.

Physiologically harmless salts can likewise be metal or ammonium salts of the compounds according to the invention which possess a free carboxyl group. Those which are particularly preferred are, for example, sodium, potassium, magnesium or calcium salts, as well as ammonium salts which are derived from ammonia, or organic amines, such as, for example, ethylamine, diethylamine, triethylamine, diethanolamine, triethanolamine, dicyclohexylamine, dimethylaminoethanol, arginine, lysine or ethylenediamine.

Within the scope of the abovementioned definition, hydroxyl protective group generally represents a protective group from the series comprising: tert-butoxydiphenylsilyl, trimethylsilyl, triethylsilyl, triisopropylsilyl, tert-butyldimethylsilyl, tert-butyldiphenylsilyl, triphenylsilyl, trimethylsilylethoxycarbonyl, benzyl, benzyloxycarbonyl, 2-nitrobenzyl, 4-nitrobenzyl, 2-nitrobenzyloxycarbonyl, 4-nitrobenzyloxycarbonyl, tert-butyl-oxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methylthiomethyl, methoxyethoxymethyl, [2-

(trimethylsilyl)ethoxy]methyl, 2-(methylthiomethoxy) ethoxycarbonyl, benzoyl, 4-methylbenzoyl, 4-nitrobenzoyl, 4-fluorobenzoyl, 4-chlorobenzoyl or 4-methoxybenzoyl. Acetyl, benzoyl, benzyl or methylbenzyl are preferred.

Within the scope of the invention, amino protective groups are the amino protective groups which are customarily used in peptide chemistry.

They preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxybenzyloxycarbonyl, cyclohexyloxycarbonyl, 1,1-dimethylethoxycarbonyl, adamantylcarbonyl, phthaloyl, 2,2,2-trichloroethoxycarbonyl, 2,2,2-trichloro-tert-butoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl, or benzyloxymethylene, 4-nitrobenzyl, 2,4-dinitrobenzyl or 4-nitrophenyl.

In general, heterocycle represents a 5- to 7-membered, preferably 5- to 6-membered, saturated or unsaturated ring which may contain, as heteroatoms, up to 3 oxygen, sulphur and/or nitrogen atoms. 5- and 6-membered rings are preferred which have an oxygen atom, a sulphur atom, and/or up to 3 nitrogen atoms. The following are mentioned as being particularly preferred: pyrrolyl, pyrazolyl, pyridyl, pyrimidyl, pyrazinyl, pyridazinyl, thiazolyl, oxazolyl, imidazolyl, isoxazolyl, pyrrolidinyl, piperidinyl, piperazinyl, tetrazolyl or morpholinyl.

The compounds of the general formula (1) according to the invention possess, as the compound of the general formula (II)

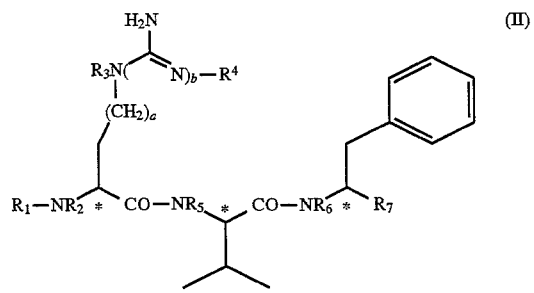

shows, at least 3 asymmetric carbon atoms (*). Independently of each other, they can exist in the D or L form, and in the R or S configuration. The invention encompasses the optical antipodes as well as the isomeric mixtures or racemates.

The compounds of the general formula (I) according to the invention can exist in stereoisomeric forms, for example those which either do (enantiomers) or do not (diastereomers) relate to each other as image and mirror image, or else as a diastereomeric mixture. The invention relates to the antipodes, racemic forms, diastereomeric mixtures and the pure isomers. The racemic forms, like the diastereomeric mixtures, can be separated, in a known manner, into the stereoisomerically homogeneous constituents.

Separation into the stereoisomerically homogeneous compounds is effected, for example, by means of chromatographic racemate resolution of diastereomeric esters and amides, or on optically active phases. Crystallization of diastereomeric salts is also possible.

Compounds of the general formula (I) are preferred in which a represents a number 2 or 3, b represents a number 0 or 1, $R^1$ represents hydrogen, tert-butoxycarbonyl (Boc), benzyloxycarbonyl (Z) or 9-fluorenylmethoxycarbonyl (FMOC), or represents a radical of the formula $R^8—NR^9—CO—$, $R^{10}—(CH_2)_c—CO—$, $R^{11}—(CH_2)_d—O—CO$, or represents a radical of the formula $—SO_2—R^{12}$, in which $R^8$ denotes cyclopentyl or cyclohexyl, or denotes straight-chain or branched alkyl having up to 16 carbon atoms which is optionally substituted by hydroxyl, methoxy, fluorine, chlorine, bromine, trifluoromethyl, trifluoromethoxy, cyclopentyl, cyclohexyl or phenyl which, for its part, can be substituted identically or differently up to 2 times by carboxyl, cyano, hydroxyl, fluorine, chlorine, bromine, perhalogenoalkyl having up to 4 carbon atoms or by straight-chain or branched acyl, alkoxy or alkoxycarbonyl having in each case up to 4 carbon atoms, or alkyl is optionally substituted by a group of the formula $—CO_2R^{13}$, in which $R^{13}$ denotes hydrogen, or straight-chain or branched alkyl or alkenyl having in each case up to 6 carbon atoms which are optionally substituted by phenyl, or $R^8$ denotes phenyl or naphthyl which is optionally substituted identically or differently up to 3 times by carboxyl, amino, fluorine, chlorine, bromine, hydroxyl, cyano, perhalogenoalkyl having up to 4 carbon atoms or by straight-chain or branched acyl, alkoxy, vinylalkoxycarbonyl or alkoxycarbonyl having in each case up to 5 carbon atoms which, for its part, is substituted by straight-chain or branched alkoxy having up to 6 carbon atoms, or denotes an amino acid radical of the formula,

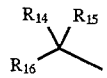

in which $R^{14}$ and $R^{15}$ are identical or different and denote hydrogen or methyl, or $R^{14}$ and $R^{15}$ together form a cyclopentyl or cyclohexyl ring, or $R^{14}$ denotes hydrogen or methyl, and $R^{15}$ denotes cyclopropyl, cyclopentyl, cyclohexyl, phenyl or hydrogen, or denotes straight-chain or branched alkyl having up to six carbon atoms, where the alkyl is optionally substituted by methylthio, hydroxyl, mercapto or guanidyl, or by a group of the formula $—NR^{17}R^{18}$ or $R^{19}—OC—$, in which $R^{17}$ and $R^{18}$, independently of each other, denote hydrogen, straight-chain or branched alkyl having up to 6 carbon atoms, or phenyl, and $R^{19}$ denotes hydroxyl, benzyloxy, alkoxy having up to 6 carbon atoms, or the above-listed group —$NR^{17}R^{18}$, or the alkyl is optionally substituted by cyclopropyl, cyclopentyl or cyclohexyl, or by phenyl which, for its part, is substituted by hydroxyl, fluorine, chlorine, bromine, nitro, alkoxy having up to 8 carbon atoms, or by the group —$NR^{17}R^{18}$, in which $R^{17}$ and $R^{18}$ have the abovementioned meanings, or the alkyl is optionally substituted by imidazolyl or indolyl, in which the corresponding —NH-functions are optionally protected by alkyl having up to 6 carbon atoms or by an amino protective group, $R^{16}$ denotes straight-chain or branched alkyl having up to 6 carbon atoms which is optionally substituted by hydroxyl or straight-chain or branched alkoxy having up to 4 carbon atoms, or denotes carboxyl, allyloxycarbonyl, straight-chain or branched alkoxycarbonyl having up to 6 carbon atoms, or benzyloxycarbonyl, $R^8$ denotes a radical of the formula,

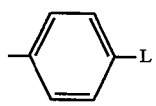

in which

L denotes phenyl or pyridyl, $R^9$ denotes hydrogen, straight-chain or branched alkyl having up to 4 carbon atoms, tert-butoxycarbonyl (Boc) or benzyloxycarbonyl (Z), $R^{10}$ denotes straight-chain or branched alkyl having up to 6 carbon atoms, phenoxy, phenyl, naphthyl, indolyl, quinolyl, quinoxalinyl, isoquinolyl, pyridyl, pyrazinyl, pyrimidyl, triazolyl or imidazolyl, where the cycles are optionally substituted identically or differently up to 3 times by nitro, carboxyl, cyano, hydroxyl, fluorine, chlorine, bromine, perhalogenoalkyl having up to 4 carbon atoms or by straight-chain or branched alkyl, acyl, alkoxy or alkoxycarbonyl having in each case up to 4 carbon atoms, or phenyl is optionally substituted by pyridyl or triazolyl, where the latter in turn can be substituted by phenyl, or $R^{10}$ denotes a radical of the formula

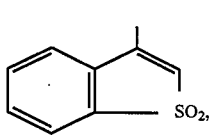

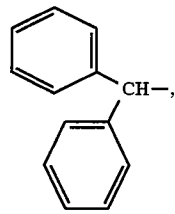

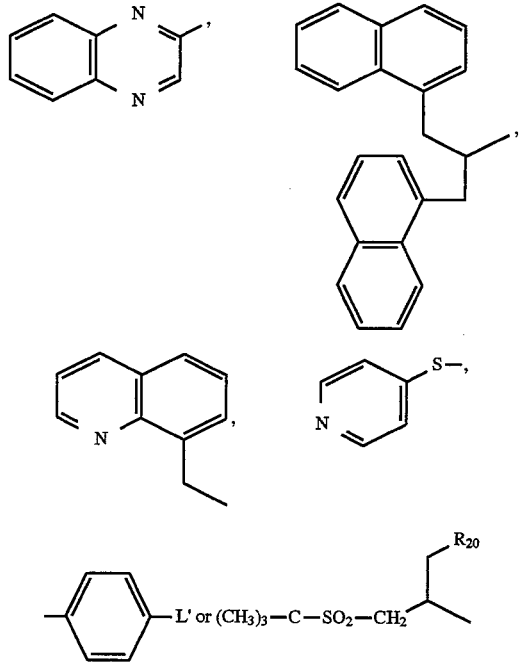

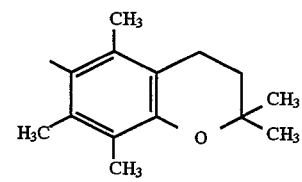

in which

L' has the abovementioned meaning of L and is identical to or different from the latter, $R^{20}$ denotes phenyl or naphthyl, c denotes a number 0, 1, 2 or 3, d denotes a number 0, 1 or 2, $R^{11}$ has the abovementioned meaning of $R^{10}$ and is identical to or different from the latter, $R^{12}$ denotes methyl or phenyl which is optionally substituted identically or differently up to 4 times by methyl or methoxy, or denotes a radical of the formula $R^2$, $R^3$, $R^5$ and $R^6$ are identical or different and denote Boc, hydrogen, methyl, ethyl, benzyloxycarbonyl or tert-butyl, $R^4$ represents hydrogen, nitro, benzyloxycarbonyl or tert-butoxycarbonyl, or represents a radical of the formula —$SO_2R^{21}$, in which $R^{21}$ has the abovementioned meaning of $R^{12}$ and is identical to or different from the latter, $R^7$ represents formyl or carboxyl, or represents straight-chain or branched alkoxycarbonyl having up to 6 carbon atoms, or represents a radical of the formula —$CH_2$—$OR^{22}$ or —$CH(OR^{23})_2$, in which $R^{22}$ and $R^{23}$ are identical or different and denote hydrogen, straight-chain or branched alkyl having up to 4 carbon atoms, acetyl or benzyl, and salts thereof, with the proviso that if a represents the number 2, b represents the number 1 and $R^5$ represents hydrogen, $R^1$ may not denote the radical of the formula $R^8$—NH—CO—.

Compounds of the general formula (1) are particularly preferred in which a represents a number 2 or 3, b represents a number 0 or 1, $R^1$ represents hydrogen, tert-butoxycarbonyl (Boc) or benzyloxycarbonyl (Z), or represents a radical of the formula $R^8$—$NR^9$—CO—, $R^{10}$—$(CH_2)_c$—CO—, $R^{11}$—$(CH_2)_d$—O—CO, or represents a radical of the formula —$SO_2$—$R^{12}$, in which $R^8$ denotes cyclopentyl or cyclohexyl, or denotes straight-chain or branched alkyl having up to 14 carbon atoms which is optionally substituted by hydroxyl, methoxy, fluorine, trifluoromethyl, trifluoromethoxy, cyclohexyl or phenyl, which is optionally substituted by a group of the formula —$CO_2R^{13}$, in which $R^{13}$ denotes hydrogen, or straight-chain or branched alkyl or alkenyl having in each case up to 4 carbon atoms, or benzyl.

or $R^8$ denotes phenyl which is optionally substituted identically or differently up to 2 times by carboxyl, fluorine, hydroxyl, cyano, trifluoromethyl or amino, or by straight-chain or branched acyl, alkoxy, vinylalkoxycarbonyl or alkoxycarbonyl having in each case up to 4 carbon atoms which, for its part, is substituted by straight-chain or branched alkoxy having up to 4 carbon atoms, or denotes an amino acid radical of the formula,

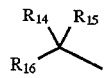

in which $R^{14}$ and $R^{15}$ are identical or different and denote hydrogen or methyl, or $R^{14}$ and $R^{15}$ together form a cyclopentyl or cyclohexyl ring, or $R^{14}$ denotes hydrogen or methyl, and $R^{15}$ denotes cyclopropyl, cyclopentyl, cyclohexyl, phenyl or hydrogen, or denotes straight-chain or branched alkyl having up to 6 carbon atoms, where the alkyl is optionally substituted by methylthio, hydroxyl, mercapto or guanidyl, or by a group of the formula —$NR^{17}R^{18}$ or $R^{19}$—OC—, in which $R^{17}$ and $R^{18}$, independently of each other, denote hydrogen, straight-chain or branched alkyl having up to 6 carbon atoms, or phenyl, and $R^{19}$ denotes hydroxyl, benzyloxy, alkoxy having up to 4 carbon atoms, or the above-listed group —$NR^{17}R^{18}$, or the alkyl is optionally substituted by cyclopropyl, cyclopentyl or cyclohexyl, or by phenyl which, for its part, is substituted by hydroxyl, fluorine, chlorine, bromine, nitro, alkoxy having up to 6 carbon atoms, or by the group —$NR^{17}R^{18}$, in which $R^{17}$ and $R^{18}$ have the abovementioned meanings, or the alkyl is optionally substituted by imidazolyl or indolyl in which the corresponding —NH— functions are optionally protected by alkyl having up to 4 carbon atoms, tert-butoxycarbonyl or benzyloxycarbonyl, $R^{16}$ denotes straight-chain or branched alkyl having up to 4 carbon atoms which is optionally substituted by hydroxyl or straight-chain or branched alkoxy having up to 3 carbon atoms, or denotes carboxyl, allyloxycarbonyl, straight-chain or branched alkoxycarbonyl having up to 4 carbon atoms, or benzyloxycarbonyl, $R^8$ denotes a radical of the formula,

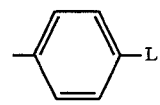

in which

L denotes phenyl or pyridyl, $R^9$ denotes hydrogen, methyl, ethyl or tert-butyl, $R^{10}$ denotes straight-chain or branched alkyl having up to 6 carbon atoms, phenoxy, phenyl, naphthyl, indolyl, quinolyl, quinoxalinyl, isoquinolyl, pyridyl, pyrazinyl, pyrimidyl, triazolyl or imidazolyl, where the cycles are optionally substituted identically or differently up to 3 times by nitro, carboxyl, cyano, hydroxyl, fluorine, chlorine, bromine, perhalogenoalkyl having up to 4 carbon atoms, or by straight-chain or branched alkyl, acyl, alkoxy or alkoxycarbonyl having in each case up to 4 carbon atoms, or phenyl is optionally substituted by pyridyl or triazolyl, where these in turn can be substituted by phenyl, or $R^{10}$ denotes a radical of the formula

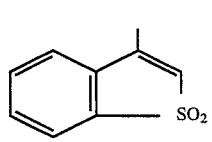 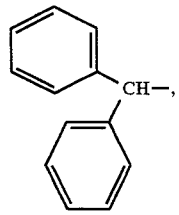

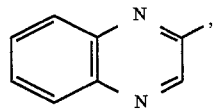 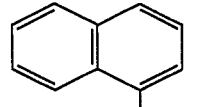

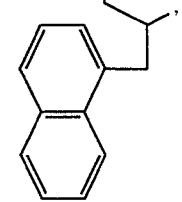

-continued

[Structures: quinoline with ethyl substituent; pyridine-S— group]

—⟨phenyl⟩—L' or (CH₃)₃—C—SO₂—CH₂—CH(R₂₀)— in which

L' has the abovementioned meaning of L and is identical to or different from the latter, $R^{20}$ denotes phenyl or naphthyl, c denotes a number 0, 1, 2 or 3, d denotes a number 0, 1 or 2, $R^{11}$ has the abovementioned meaning of $R^{10}$ and is identical to or different from the latter, $R^{12}$ denotes methyl or phenyl which is optionally substituted identically or differently up to 4 times by methyl or methoxy, or denotes a radical of the formula

[Structure: tetramethyl-substituted benzofuran-type ring with gem-dimethyl]

$R^2$, $R^3$, $R^5$ and $R^6$ are identical or different and denote Boc, hydrogen, methyl, ethyl, benzyloxycarbonyl or tert-butyl, $R^4$ represents hydrogen, nitro, benzyloxycarbonyl or tert-butoxycarbonyl, or represents a radical of the formula —SO₂$R^{21}$, in which $R^{21}$ has the abovementioned meaning of $R^{12}$ and is identical to or different from the latter, $R^7$ represents formyl or carboxyl, or represents straight-chain or branched alkoxycarbonyl having up to 4 carbon atoms, or represents a radical of the formula —CH₂—O$R^{22}$ or —CH(O$R^{23}$)₂, in which $R^{22}$ and $R^{23}$ are identical or different and denote hydrogen, straight-chain or branched alkyl having up to 3 carbon atoms, or benzyl, and salts thereof, with the proviso that if a represents the number 2, b represents the number 1 and $R^5$ represents hydrogen, $R^1$ may not represent the radical of the formula $R^8$—NH—CO—.

In addition, processes have been found for preparing the compounds of the general formula (I) according to the invention, which processes are characterized in that compounds of the general formula (III)

[Structure III: 2HCl × HNR₂—CH(CH₂)ₐ—N(R₃)(Nb—R⁴')—C(=NH)NH₂ backbone with CO—NR₅—CH(iPr)—CO—NR₆—CHR₇—CH₂-phenyl]

$$\text{(III)}$$

in which a, b, $R^2$, $R^3$, $R^5$, $R^6$ and $R^7$ have the abovementioned meanings, and $R^{4"}$ has the abovementioned meaning of $R^4$ but does not represent hydrogen,

[A] in the case where $R^1$ represents the radical of the formula $R^8$—$NR^9$—CO—, are first converted, by reaction with compounds of the general formula (IV)

$$R^8\text{—N=C=O} \quad \text{(IV)}$$

in which $R^8$ has the abovementioned meanings, in inert solvents and in the presence of a base, into the compounds of the general formula (V)

[Structure V: R₈—NH—CO—NR₂—CH(CH₂)ₐ—N(R₃)(Nb—R⁴')—C(=NH)NH₂ backbone with CO—NR₅—CH(iPr)—CO—NR₆—CHR₇—CH₂-phenyl]

$$\text{(V)}$$

in which a, b, $R^1$, $R^2$, $R^3$, $R^5$, $R^6$, $R^7$ and $R^8$ have the abovementioned meanings, or

[B] in the case where $R^1 \neq R^8$—NH—CO—, compounds of the general formula (III) are reacted with compounds of the general formula (VI) or (VII)

$$V\text{—CO—}W \quad \text{(VI)}$$

or $$X\text{—SO}_2\text{—}R^{12} \quad \text{(VII)}$$

in which $R^{12}$ has the abovementioned meaning,

V encompasses the above-listed scope of meaning of the radicals $R^{10}$—(CH₂)$_c$ or $R^{11}$—(CH₂)$_d$—O—, and W and X are identical or different and denote hydroxyl, or a typical carboxylic acid-activating radical, such as, for example, chlorine, in accordance with the methods which are customary in peptide chemistry, in inert organic solvents and in the presence of a base and an auxiliary agent, and, in the case where $R^2$, $R^3$, $R^5$, $R^6$ and $R^9 \neq H$, this is optionally followed by an alkylation in accordance with customary methods, and, in the case where $R^7=CH_2-OH$, the compounds of the general formula (V) ($R^7=COOCH_3$) are reacted in accordance with customary methods, preferably, however, with sodium borohydride, and, in the case where $R^7=CHO$, the compounds of the general formula (V) are subjected to an oxidation, starting from the hydroxymethyl compound ($R^7=CH_2-OH$), depending on the radical $R^{4'}$, reaction takes place, for example, with hydrofluoric acid or trifluoroacetic acid to give $R^4=H$, and, in the case of an amino protective group ($R^1$, $R^2$, $R^3$, $R^4$, $R^5$ and $R^6$), this is eliminated in accordance with the methods which are customary in peptide chemistry, and, in the case of the acids, the esters are hydrolyzed.

The process according to the invention may, by way of example, be illustrated by the following formula schemes (schemes 1–3):

Scheme 1

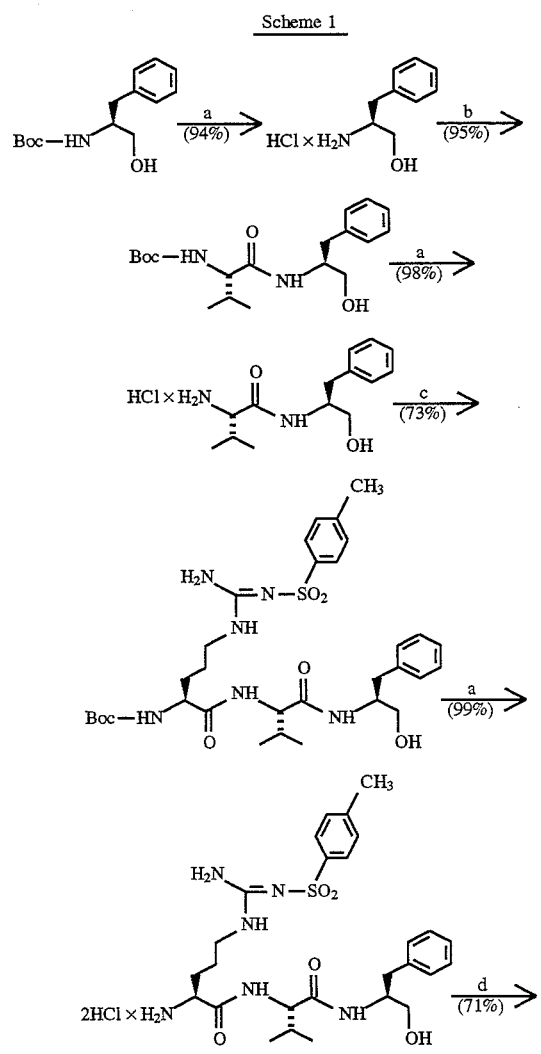

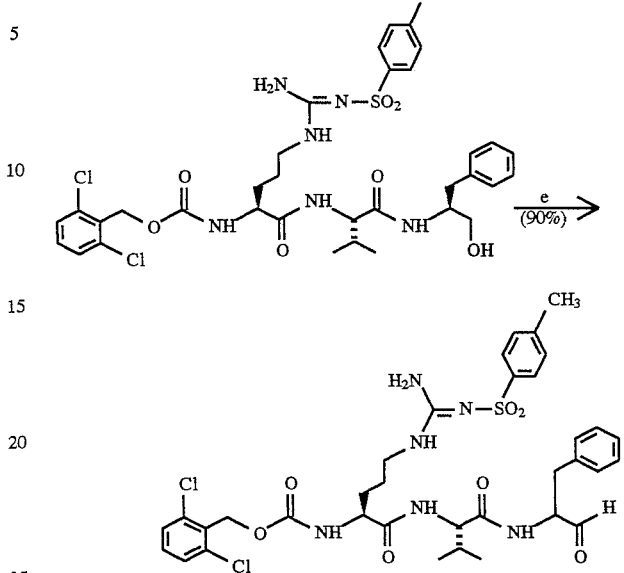

Reagents:

a) 4N HCl in dioxane; room temperature for 30 min.
b) Boc-Gly(t-Bu)-OH, HOBT, DCC, $CH_2Cl_2$; room temperature for 2 h
c) Boc-Arg (Tos)-OH, HOBT, DCC, $CH_2Cl_2$/DMF; room temperature for 1 h
d) 2,6-Cl-$C_6H_4$-$CH_2$OCOCl, dioxane, water, pH 9–10, room temperature for 2 h
e) PyrxSO$_3$, NEt$_3$, DMSO, room temperature for 1 h

Scheme 2

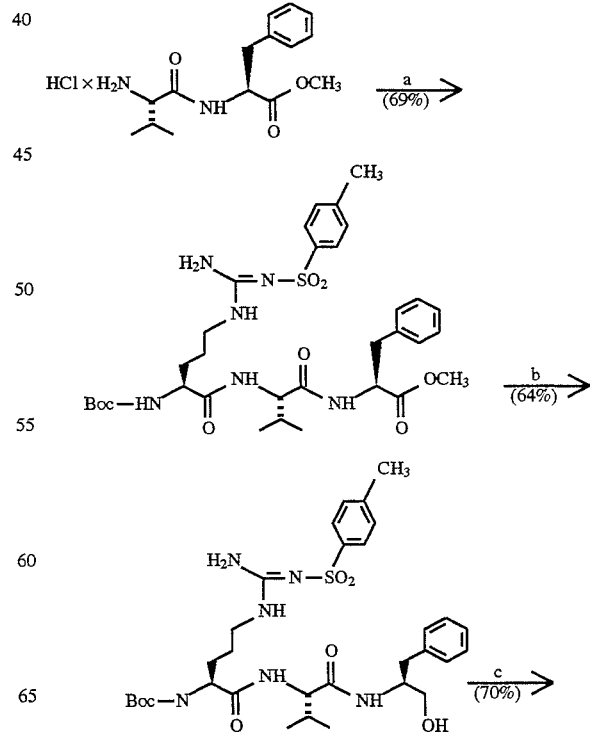

-continued
Scheme 2
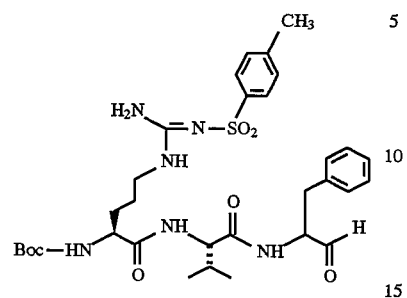
Reagents:
a) Boc-Arg(Tos)-OH, BOBT, DCC, CH$_2$Cl$_2$, DMF, room temperature for 1 h
b) NaBH$_4$, LiI, THF, MeOH, 40° C. for 5 h
c) PyrxSO$_3$, NEt$_3$, DMSO, room temperature for 1 h
Scheme 3
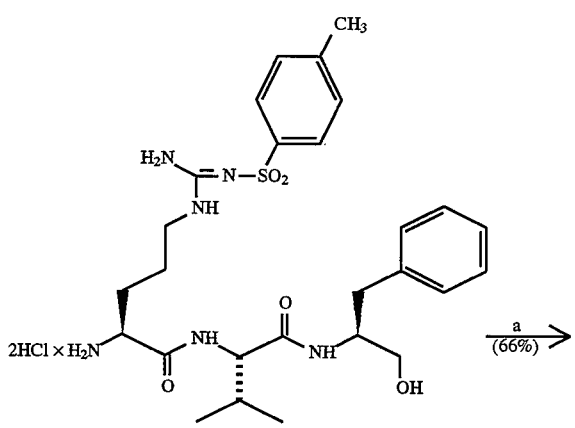
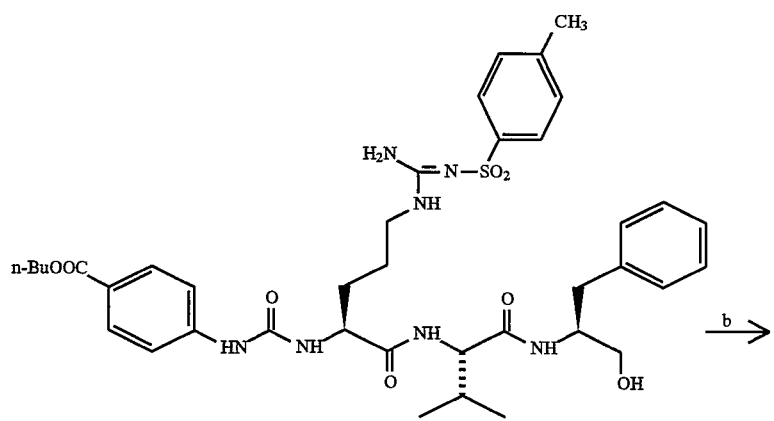

-continued
Scheme 3

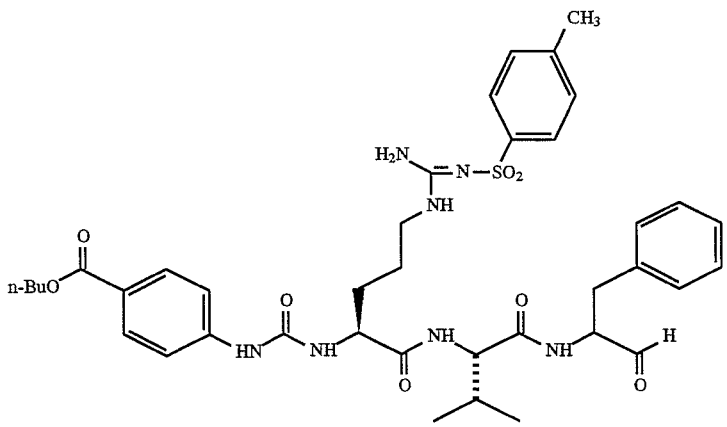

20

Reagents:
a) n-BuOCO-C₆H₄-NCO, NEt₃, CH₂Cl₂; room temperature for 30 min
b) PyrxSO₃, NEt₃, DMSO, room temperature for 1 h The customary inert solvents which are not altered under the reaction conditions can suitably be used as solvents for all procedural steps. These solvents preferably include organic solvents, such as ethers, e.g. diethyl ether, glycol monomethyl ether, glycol dimethyl ether, dioxane or tetrahydrofuran, or hydrocarbons, such as benzene, p-cresol, toluene, xylene, cyclohexane or petroleum fractions, or halogenohydrocarbons, such as methylene chloride, chloroform or carbon tetrachloride, or dimethyl sulphoxide, dimethylformamide, hexamethylphosphoric triamide, ethyl acetate, pyridine, triethylamine or picoline. It is likewise possible to use mixtures of the said solvents, optionally also together with water. Methylene chloride, tetrahydrofuran, dioxane and dioxane/water are preferred.

Suitable bases are organic amines (trialkyl($C_1$–$C_6$) amines, such as, for example, triethylamine, or heterocycles, such as pyridine, methylpiperidine, piperidine or N-methylmorpholine. Triethylamine and N-methylmorpholine are preferred.

In general, the bases are employed in a quantity of from 0.1 mol to 5 mol, preferably of from 1 mol to 3 mol, in each case based on 1 mol of the compounds of the general formula (III), (VI) and (VII).

The reactions can be carried out under atmospheric pressure, and also at elevated or reduced pressure (e.g. from 0.5 to 3 bar). In general, atmospheric pressure is employed.

The reactions are carried out in a temperature range of from 0° C. to 100° C., preferably at from 0° C. to 30° C., and under atmospheric pressure.

The amino protective groups are eliminated in a manner known per se.

In general, the tosyl group is eliminated using hydrofluoric acid (anhydrous) in the presence of a scavenger, preferably p-cresol, or using pyridinium hydrofluoride [see Matsuura et al., J. C. S. Chem. Comm. (1976), 451], in a temperature range of from −10° C. to +30° C., preferably at 0° C.

Condensing agents, which may also be bases, are preferably employed as auxiliary substances for the respective peptide couplings, particularly if the carboxyl group is present in activated form as an anhydride. In this context, the customary condensing agents, such as carbodidiimides, e.g. N,N'-diethylcarbodiimide, N,N'-dipropylcarbodiimide, N,N'-diisopropylcarbodiimide, N,N'-dicyclohexylcarbodiimide and N-(3-dimethylaminoisopropyl)-N'-ethylcarbodiimide hydrochloride, or carbonyl compounds, such as carbonyldiimidazole, or isoxazolium compounds, such as 2-ethyl-5-phenyl-isoxazolium-3-sulphate or 2-tert-butyl-5-methyl-isoxazolium perchlorate, or acylamino compounds, such as 2-ethoxy-1-ethoxycarbonyl-1,2-dihydroquinoline, or propylphosphonicanhydride, or isobutyl chloroformate, or bis-(2-oxo-3-oxazolidinyl)phosporyl chloride, or benzotriazolyloxy-tris(dimethylamino)phosphonium hexafluorophosphate, or 1-hydroxybenzotriazole, and, as bases, alkali metal carbonates, e.g. sodium or potassium carbonate, or sodium or potassium hydrogen carbonate, or organic bases, such as trialkylamines, e.g. triethylamine, N-ethylmorpholine, N-methylpiperidine or diisopropylethylamine, are preferably employed. Dicyclohexylcarbodiimide, N-methylmorpholine and 1-hydroxybenzotriazole are particularly preferred.

The carboxylic esters are hydrolyzed in accordance with customary methods by treating the esters with customary bases in inert solvents, it being possible to convert the salts which initially arise into the free carboxylic acids by treating with acid.

The customary inorganic bases may suitably be used as bases for the hydrolysis. These bases preferably include alkali metal hydroxides or alkaline earth metal hydroxides, such as, for example, sodium hydroxide, lithium hydroxide, potassium hydroxide or barium hydroxide, or alkali metal carbonates, such as sodium or potassium carbonate, or sodium hydrogen carbonate, or alkali metal alcoholates, such as sodium ethanolate, sodium methanolate, potassium ethanolate, potassium methanolate or potassium tert-butanolate. Sodium hydroxide or lithium hydroxide are particularly preferably employed.

Water, or the organic solvents which are customary for a hydrolysis, can suitably be used as solvents for the hydrolysis. These solvents preferably include alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is likewise possible to employ mixtures of the same solvents. Water/tetrahydrofuran is preferred.

In general, the hydrolysis is carried out in a temperature range of from 0° C. to +100° C., preferably of from 0° C. to +40° C.

In general, the hydrolysis is carried out under atmospheric pressure. However, it is also possible to carry it out under reduced pressure or under elevated pressure (e.g. from 0.5 to 5 bar).

When carrying out the hydrolysis, the base or the acid is generally employed in a quantity of from 1 to 3 mol, preferably of from 1 to 1.5 mol, based on 1 mol of the ester. Molar quantities of the reactants are particularly preferably used.

When carrying out the reaction, the salts of the compounds according to the invention arise in the first step as intermediates which can be isolated. The acids according to the invention are obtained by treating the salts with customary inorganic acids. The latter preferably include mineral acids, such as, for example, hydrochloric acid, hydrobromic acid, sulphuric acid, citric acid or phosphoric acid. When preparing the carboxylic acids, it has been found to be advantageous to acidify the basic reaction mixture of the hydrolysis in a second step without isolating the salts. The acids can then be isolated in a customary manner.

In general, the reductions can be carried out with hydrogen in water or in inert organic solvents such as alcohols, ethers or halogenohydrocarbons, or mixtures thereof, using catalysts such as Raney nickel, palladium, palladium on animal charcoal, or platinum, or using hydrides or boranes in inert solvents, optionally in the presence of a catalyst.

The reduction is preferably carried out using hydrides, such as complex borohydrides or aluminium hydrides. In this context, sodium borohydride, lithium aluminium hydride or sodium cyanoborohydride are particularly preferably employed.

In this context, all inert organic solvents which are not altered under the reaction conditions are suitable for use as solvents. They preferably include alcohols, such as methanol, ethanol, propanol or isopropanol, or ethers, such as diethyl ether, dioxane, tetrahydrofuran, glycol dimethyl ether or diethylene glycol dimethyl ether, or amides, such as hexamethylphosphoric triamide or dimethylformamide, or acetic acid. It is likewise possible to use mixtures of the said solvents. Methanol and tetrahydrofuran are preferred.

Potassium or lithium iodide, preferably lithium iodide, may also be employed as catalysts in the reductions.

In general, the catalyst is employed in a quantity of from 0.1 mol to 5 mol, preferably of from 1 mol to 3 mol, in each case based on 1 mol of the ester to be reduced.

The reaction may be carried out under atmospheric, elevated or reduced pressure (e.g. 0.5 to 5 bar). In general, atmospheric pressure is employed.

In general, the reductions are carried out in a temperature range of from 0° C. to +60° C., preferably at from +10° C. to +40° C.

In general, alcohol groups are oxidized to the corresponding aldehydes in one of the above-listed solvents, and in the presence of one of the above-listed bases, using oxidizing agents, such as, for example, potassium permanganate, bromine, Jones reagent, pyridinium dichromate, pyridinium chlorochromate or pyridine sulphur trioxide complex, or using sodium hypochlorite and 2,2,6,6-tetramethylpiperidin-1-oxyl (TEMPO) [Org. Synth. 69, 212 (1990)] or oxalyl chloride [Swern oxidation (ClCOCOCl/DMSO/CH$_2$Cl$_2$/ NEt$_3$), e.g. in accordance with R. E. Ireland et al., J. Org. Chem. 50, 2199 (1985)]. Preferably, the oxidation is effected using pyridine sulphur trioxide complex in dimethyl sulphoxide and in the presence of triethylamine.

In general, the oxidation is effected in a temperature range of from 0° C. to +50° C., preferably at room temperature and under atmospheric pressure.

The alkylation is carried out in the above-listed solvents at temperatures of from 0° C. to +150° C., preferably at from +20° C. to +100° C., and under atmospheric pressure.

Customary organic solvents which are not altered under the reaction conditions may likewise be used as solvents for the alkylation. These solvents preferably include ethers, such as diethyl ether, dioxane, tetrahydrofuran or glycol dimethyl ether, or hydrocarbons, such as benzene, toluene, xylene, hexane, cyclohexane or petroleum fractions, or halogenohydrocarbons, such as dichloromethane, trichloromethane, tetrachloromethane, dichloroethylene, trichloroethylene or chlorobenzene, or ethyl acetate, or triethylamine, pyridine, dimethyl sulphoxide, dimethylformamide, hexamethylphosphoric triamide, acetonitrile, acetone or nitromethane. It is likewise possible to use mixtures of the said solvents. Dimethylformamide is preferred. Sodium hydride may also be employed as a base in the alkylation.

The compounds of the general formula (III) are, for the most part, novel and can then be prepared, in accordance with the methods which are customary in peptide chemistry, by, for example, reacting compounds of the general formula (VIII)

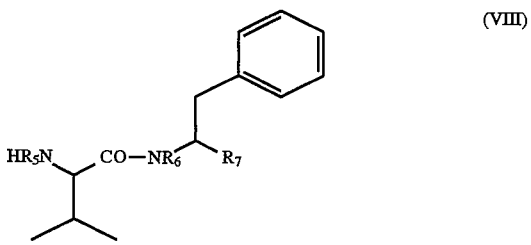

in which

R$^5$, R$^6$ and R$^7$ have the abovementioned meanings, with the amino acid derivatives of the formula (IX)

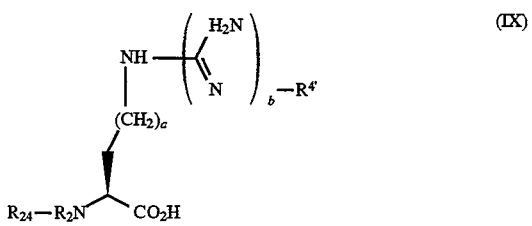

in which a, b, R$^2$ and R$^{4'}$ have the abovementioned meanings, and

R$^{24}$ represents one of the abovelisted amino protective groups, preferably 9-fluorenylmethoxycarbonyl (Fmoc), tert-butoxycarbonyl (Boc), or benzyloxycarbonyl (Z), in one of the abovementioned solvents, preferably methylene chloride, and in the presence of an auxiliary substance and/or a base, preferably HOBT and dicyclohexylcarbodiimide, and, subsequently, likewise in accordance with customary methods, eliminating the amino protective group, Boc preferably being eliminated with hydrochloric acid in dioxane, Fmoc preferably with piperidine, and Z preferably with HBr/HOAc or by hydrogenolysis.

All procedural steps are carried out under atmospheric pressure and in a temperature range of from 0° C. to room temperature, preferably at room temperature.

The compounds of the general formulae (VIII) and (IX) are, for the most part, known, or can be prepared in accordance with customary methods [cf. J. Chem. Res., Synop., (2), 62–63; DE 36 04 510].

The compounds of the general formula (V) are likewise known [cf. U.S. Pat. No. 4,929,736].

The compounds of the general formulae (VI) and (VII) are known.

The compounds exhibit an antiviral effect towards retroviruses and representatives of the Herpetoviridae group, in particular towards human cytomegalovirus (HCMV).

The anti-HCMV effect was determined in a screening test system in 96-well microtitre plates with the aid of human embryonic lung fibroblast (HELF) cell cultures. The influence of the substances on the spread of the cytopathogenic effect was compared with that of the reference substance ganciclovir (Cymevene® sodium), a clinically approved anti-HCMV chemotherapeutic agent.

The substances, dissolved (50 mM) in DMSO (dimethyl sulphoxide), are investigated on microtitre plates (96-well) at final concentrations of 1000–0.00048 µM (micromolar) in double determinations (4 substances/plate). In this test, both the toxic and cytostatic effects of the substances are recorded. After the corresponding substance dilutions (1:2) have been made on the microtitre plate, a suspension of 50–100 HCMV-infected HELF cells and $3\times10^4$ non-infected HELF cells in Eagle's MEM (minimal essential medium) containing 10% foetal calf serum is added to each well and the plates are then incubated at 37° C. in a $CO_2$ incubator for a period of 6 days. At the end of this time, the cell lawn in the substance-free virus controls is, starting from 50–100 infectious centres, completely destroyed by the cytopathogenic effect (CPE) of the HCMV (100% CPE). After staining with neutral red and fixing with formalin/methanol, the plates are evaluated using a projection microscope (plaque viewer). The results for some compounds are summarized in the following table:

TABLE

Anti-HCMV (Davis) activity and anti-cellular effect

| Ex. No. | $CIC_{50}(\mu M)$[1] (HELF) | $IC_{50}(\mu M)$[2] (HCMV) | SI[3] |
|---|---|---|---|
| 46 | 0.78 | 0.03 | 25 |
| 48 | 0.21 | 0.027 | 8 |
| 50 | 28 | 7.8 | 4 |
| 52 | 19.5 | 0.15 | 130 |
| 53 | 2.9 | 0.013 | 223 |
| 54 | 3.3 | 0.081 | 40 |
| 55 | 16.9 | 0.092 | 184 |
| 56 | 5.2 | 0.043 | 121 |
| 57 | 9.8 | 0.051 | 192 |
| 58 | 67.7 | 0.45 | 150 |
| 59 | 3.4 | 0.023 | 148 |
| 61 | 0.52 | 0.0011 | 470 |
| 63 | 5.52 | 0.028 | 197 |
| 66 | 4.38 | 0.041 | 107 |
| 67 | 0.77 | 0.0064 | 120 |
| Cymevene$^R$Na | 125 | 2–4 | 32–64 |

[1] $CIC_{50}$ = highest concentration at which no obvious anti-cellular effect is evident.
[2] $IC_{50}$ = concentration of the compound according to the invention which elicits 50% inhibition of the CPE.
[3] $SI = \dfrac{CIC_{50}}{IC_{50}}$ = selectivity index It was now found that the compounds according to the invention inhibit the replication of HCMV in HELF cells at concentrations which are in some cases 10–50 times lower than that of Cymevene® sodium, and exhibit a selectivity index which is several times higher.

The compounds according to the invention thus represent valuable active compounds for the treatment and prophylaxis of diseases caused by human cytomegalovirus. The following indications may be mentioned by way of example:

1) Treatment and prophylaxis of cytomegalovirus infections in patients who are undergoing bone marrow and organ transplantations and who often contract life-threatening HCMV pneumonitis or HCMV encephalitis, as well as gastrointestinal and systemic HCMV infections.

2) Treatment and prophylaxis of HCMV infections in AIDS patients (retinitis, pneumonitis and gastrointestinal infections).

3) Treatment and prophylaxis of HCMV infections in pregnant women, the new born and small children.

In addition to this, it was found, surprisingly, that the compounds of the general formula (I) exhibit an effect against retroviruses. This is verified using a HIV-specific protease enzyme test.

The results for the examples listed below were obtained using the HIV test system described in the following literature reference [cf. Hansen, J., Billich, S., Schulze, T., Sukrow, S. and Mölling, K. (1988), EMBO Journal, Vol. 7, No. 6, pp. 1785–1791]: purified HIV protease was incubated together with synthetic peptide which imitates a cleavage site in the gag precursor protein and represents an in-vivo cleavage site for protease. The resulting cleavage products from the synthetic peptide were analysed by reverse phase high performance liquid chromatography (RP-HPLC). The $IC_{50}$ values which are given refer to the substance concentration which elicits 50% inhibition of the protease activity under the above-listed test conditions.

TABLE

| | $IC_{50}$ (RP-HPLC) (µM) |
|---|---|
| Ex. No. | HIV-1 |
| 22 | 18 |
| 61 | 7.3 |
| 64 | 0.19 |
| 66 | 0.22 |
| 68 | 1.1 |
| 69 | 30 |

The novel active compound can, in a known manner, be converted into the customary formulations, such as tablets, coated tablets, pills, granules, aerosols, syrups, emulsions, suspensions and solutions, using inert, non-toxic, pharmaceutically suitable excipients or solvents. In this context, the therapeutically active compound should in each case be present at a concentration of about 0.5 to 90% by weight of the total mixture, i.e. in quantities which are sufficient to achieve the given dosage scope.

The formulations are prepared, for example, by extending the active compounds with solvents and/or excipients, optionally using emulsifiers and/or dispersants, it being possible, where appropriate, for example when using water as a diluent, to use organic solvents as solubilizing agents.

Administration is effected in a customary manner, preferably orally, parenterally or topically, especially perlingually or intravenously.

For parenteral applications, solutions of the active compound can be employed in association with the use of suitable liquid carrier materials.

In general, it has been found to be advantageous, in the case of intravenous administration, to administer quantities of about 0.001 to 10 mg/kg, preferably about 0.01 to 5 mg/kg, of body weight in order to achieve efficacious results.

and, in the case of oral administration, the dosage is about 0.01 to 25 mg/kg, preferably 0.1 to 10 mg/kg, of body weight.

Despite this, it can, where appropriate, be necessary to diverge from the said quantities, specifically in dependence on the body weight and the nature of the route of administration, on the individual response to the medicament, on the nature of its formulation and on the time and interval at which administration is effected. Thus, in some cases, it can be sufficient to make do with less than the abovementioned lowest quantity, while, in other cases, the said upper limit must be exceeded. Where relatively large quantities are being administered, it can be advisable to divide these into several smaller doses which are given over the course of the day.

The compounds according to the invention may be employed as enzyme inhibitors in all areas which are generally known for inhibitors. This means, for example, their employment as affinity labels for affinity chromatography in the purification of proteases. They can also serve as aids for clarifying enzyme reaction mechanisms and for improving the specificity of diagnostic methods.

Appendix to the experimental section
I. Amino acids

In general, the configuration is designated by placing a L or D in front of the amino acid abbreviation, in the case of the racemate by a D, L -, it being possible, for simplicity, to omit the configuration in the case of L-amino acids, and then only to give a more explicit designation in the case of the D form and/or the D,L mixture.

| Ala | L-alanine |
| Arg | L-arginine |
| Ile | L-isoleucine |
| Leu | L-leucine |
| Phe | L-phenylalanine |
| Val | L-valine |
| Gly | glycine |
| Orn | L-ornithine |
| Lys | L-lysine |

—Gly(t-Bu)—

—NCH₃—Val— 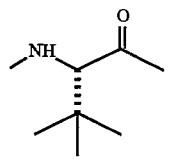

—NCH₃—Ile— 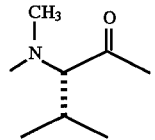

—NCH₃—Ala— 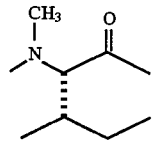

—NCH₃—Gly— 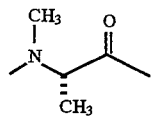

—βAla— 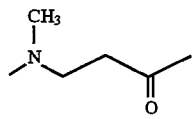

—Aib— 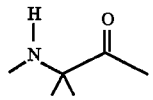

—Arg(Tos)— 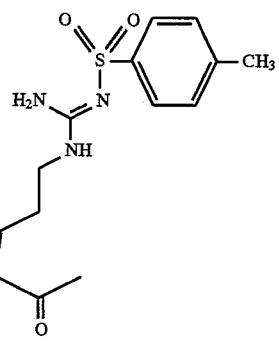

—Arg(NO₂)— 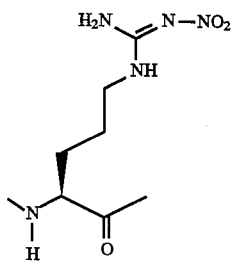

—Lys(Tos)— 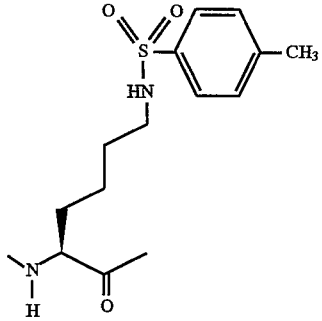

—Orn(Z)— 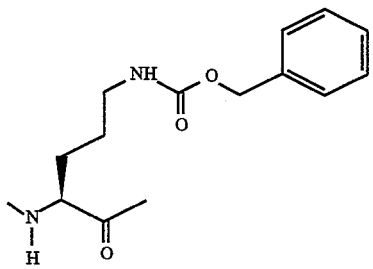

II. Abbreviations
Z benzyloxycarbonyl
Boc tert-butyloxycarbonyl
CMCT 1-cyclohexyl-3-(2-morpholino-ethyl)carbodiimide metho-p-toluenesulphonate
DCC dicyclohexylcarbodiimide
DMF dimethylformamide
HOBT 1-hydroxybenzotriazole
Ph phenyl THF tetrahydrofuran
DMSO dimethyl sulphoxide
Fmoc 9-fluorenylmethoxycarbonyl
III. List of the Eluent Mixtures Used for the Chromatography
I: Dichloromethane:methanol
II: Toluene:ethyl acetate
III: Acetonitrile:water Starting Compounds Example I (2S )-2-Amino-3-phenyl-propan-1-ol hydrochloride

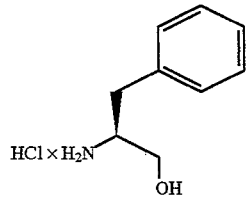

A solution of 20.10 g (80.00 mmol) of (S)-2-(tert-butoxycarbonylamino-1-phenyl-propan-1-ol [J. Med. Chem. 33, 2707 (1990)] in 200 ml of a 4N solution of gaseous hydrogen chloride in anhydrous dioxane is stirred at room temperature for 30 min. After that, 60 ml of toluene are added and the mixture is concentrated in vacuo. This process is repeated a further two times and the residue is then triturated with a little ether, filtered off with suction and dried under high vacuum over KOH. 14.14 g (94% of theory) of the title compound are obtained as colourless crystals.

M.p.: 148°–150° C. (ether) $R_f$=0.25 (acetonitrile:water 9:1) MS (DCI, $NH_3$) m/z=152 (M+H)$^+$ IR (KBr) 3357, 2928, 1571, 1495, 1456, 1026, 738, 708 cm$^{-1}$ $[\alpha]^{20}_D$=–4.2° (c=2.94, $CH_3OH$) $^1$H-NMR (300 MHz, $CD_3OD$) δ=2.95 (d, 2H, J=7.5 Hz, $CH_2$); 3.50 (m, 2H); 3.70 (m, 1H); 7.30 (m, 5H,Ph). $C_9H_{13}NO×HCl$ (187.67)

EXAMPLE II (2S )-2-[N-(tert-butoxycarbonyl)-5-valinyl]amino-3-phenylpropan-1-ol

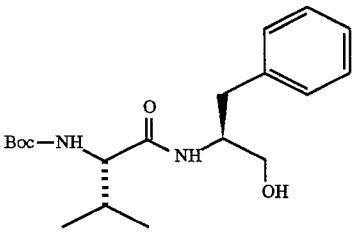

16.32 g (79.10 mmol) of DCC are added to a solution, which is cooled to 0° C. and stirred, of 18.01 g (82.90 mmol) of N-(tert-butoxycarbonyl)-L-valine and 12.69 g (82.90 mmol) of HOBT in 300 ml of anhydrous dichloromethane, and the mixture is then stirred for 5 min. After this, a solution of 14.14 g (75.40 mmol) of the compound from Example I and 20.73 g (188.50 mmol) of N-methylmorpholine in 300 ml of dichloromethane is added dropwise. The cooling bath is removed and the reaction mixture is left stirring at room temperature for 2 h. The end of the reaction is established by thin layer chromatography. The resulting urea is separated off by filtration, and the filtrate is concentrated in vacuo and the crude product is purified by chromatography on 450 g of silica gel (dichloromethane:methanol 95:5). 25.15 g (95% of theory) of the title compound are obtained as colourless crystals.

M.p.: 143° C. $R_f$=0.29 (dichloromethane:methanol 95:5) MS (FAB) m/z=351 (M+H)$^+$ IR (KBr) 3340, 2933, 1686, 1657, 1523, 1368, 1311, 1246, 1172, 1044, 698 cm$^{-1}$ $[\alpha]^{20}_D$=–42.1° (c=0.401, $CH_3OH$) $^2$H-NMR (300 MHz, $CD_3OD$)δ=0.87 (t, J=7 Hz, 6H [$CH_3$]$_2$CH); 1.44 (s, 9H, $CH_3$—C); 1.93 (m, 1H, [$CH_3$]$_2$CH); 2.74 (dd, J=8, 14 Hz, 1H, $CH_2$Ph); 3.92 (dd, J=6 Hz, 14 Hz, 1H $CH_2$Ph); 3.50 (d, J=6 Hz, 2H, $CH_2$OH); 3.79 (d, J=7 Hz, 1H, NCHCO); 4.12 (m, 1H, NCH); 7.23 (m, 5H, Ph). $C_{19}H_{30}N_2O_4$ (350.47)

The compound listed in Table I is obtained, as described for Example II, by condensing the compound from Example I with the corresponding N-saturated amino acids:

TABLE I

| Ex. No. | R$^{10}$ | Yield (% of theory) | MS (FAB) m/z(M + H)$^+$ | R$_f$/eluent ratio | M.p. (°C.) |
| --- | --- | --- | --- | --- | --- |
| III | CH$_3$ \| Boc—N | 89 | 365 | 0.48, I (9:1) | Oil |

EXAMPLE IV (2S)-2-(N-S-Valinyl)amino-3-phenyl-propan-1-ol

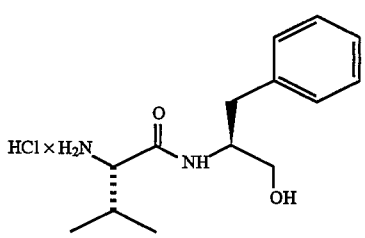

180 ml of a 4N solution of gaseous hydrogen chloride in anhydrous dioxane are added to a solution of 25.15 g (75.6 mmol) of the compound from Example I in 180 ml of anhydrous dioxane, and the mixture is then stirred at room temperature for 30 min. After this, 150 ml of toluene are added and the mixture is concentrated in vacuo. This procedure is repeated a further two times and the residue is then triturated with 300 ml of ether, filtered off with suction, and dried under high vacuum over KOH. 20.12 g (98% of theory) of the title compound are obtained as colourless crystals.

M.p.: from 100° C. (decomp.) $R_f$=0.19 (acetonitrile:water 9:1) MS (DCI, $NH_3$) m/z=251 $(M+H)^+$ IR (KBr) 3267, 2931, 1670, 1571, 1496, 1259, 1120, 1040, 870 $cm^{-1}$ $[\alpha]^{20}_D$=2.5° (c=0.375, $CH_3OH$) $^1$H-NMR (300 MHz, $CDCl_3$) δ=1.03, 1.07 (d, 7 Hz, 6H, [$CH_3$]$_2$CH); 2.20 (m, 1H, [$CH_3$]$_2$CH); 2.88 (AB, J=7.5, 15 Hz, 2H, $CH_2$Ph); 3.54 (m, 2H, $CH_2$OH); 3.63 (d, J=6.5 Hz, 1H, NCHCO); 4.16 (1H, NCH); 7.28 (m, 5H, Ph). $C_{14}H_{22}N_2O_2$×HCl (286.80) Calc.: C 58.63 H 8.08 N 9.77 Found: C 58.7 H 8.3 N 9.5

The hydrochloride listed in Table II is obtained, as described for Example I, after elimination of the amino protective group from the compound described in Table I:

EXAMPLE VI (2S)-2-[Nα-(tert-Butoxycarbonyl)-$N^G$-(4-methyl-phenylsulphonyl)-S-arginyl-S-valinyl]amino-3-phenyl-propan-1-ol

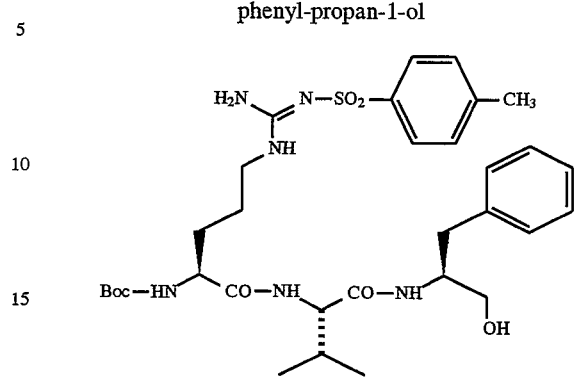

Method A:

8.57 g (41.50 mmol) of DCC are added to a solution, which is cooled to 0° C. and stirred, of 18.64 g (43.51 mmol) of $N_g$-(tert-butoxycarbonyl)-$N^G$-(4-methylphenylsulphonyl)-S-arginine and 6.66 g (43.50 mmol) of HOBT in 190 ml of anhydrous dichloromethane and 19 ml of DMF, and the mixture is then stirred for 5 min. After this, a solution of 11.33 g (39.50 mmol) of the compound from Example IV and 17.38 ml (158.10 mmol) of N-methylmorpholine in 113 ml of dichloromethane and 11 ml of DMF is added dropwise. The cooling bath is removed and the reaction mixture is left stirring at room temperature for 1 h. The end of the reaction is established by thin layer chromatography. The resulting urea is separated off by filtration and the filtrate is concentrated in vacuo and the crude product is purified by chromatography on 500 g of silica gel (dichloromethane:methanol 9:1). 18.98 g (73% of theory) of the title compound are obtained as a colourless foam.

$R_f$=0.35 (dichloromethane:methanol 9:1) MS (FAB) m/z=661 $(M+H)^+$ IR (KBr) 3336, 2967, 1654, 1544, 1253, 1168, 1131, 1082, 676 $cm^{-1}$ $[\alpha]^{20}_D$=-32.7° (c=0.895, $CH_3OH$) $^1$H-NMR (250 MHz, $CD_3OD$) δ=0.89 (m, 6H, [$CH_3$]$_2$CH); 1.43 (s, 9H, $CH_3$—C); 1.4–1.6 (m, 4H, $CH_2$);

TABLE II

| Ex. No. | $R^{10}$ | Yield (% of theory) | MS (FAB) m/z(M + H)$^+$ | $R_f$/eluent ratio | (°C.) |
|---------|----------|---------------------|-------------------------|--------------------|-------|
| V | CH$_3$<br>\|<br>HN⤳ | 67 | 265 | 0.05, I (85:15) | 244 |

1.99 (m, 1H, [CH$_3$]$_2$CH); 2.38 (s, 3H, CH$_3$); 2.70 (dd, J=10, 16 Hz, 1H, CH$_2$Ph); 2.90 (dd, J=7.5, 15 Hz, 1H, CH$_2$Ph); 3.13 (m, 2H, CH$_2$N); 3.50 (d, J=7 Hz, 2H, CH$_2$O); 3.72 (m, 1H, NCHCO); 4.0–4.2 (m, 2H, NCHCO, NCH); 7.20 (m, 5H, Ph); 7.30, 7.73 (AB, J=10 Hz, 4H, H arom.) C$_{32}$H$_{48}$N$_6$O$_7$S (660.85) Calc.: C 58.16 H 7.32 N 12.72 Found: C 58.3 H 7.4 N 12.6

Method B:

5.51 g (8.00 mmol) of the compound from Example VIII are added in portions, within 10 min, to a solution, which is stirred and heated to 40° C., of 454 mg (12.00 mmol) of sodium borohydride and 1.61 g (12.00 mmol) of lithium iodide in 30 ml of THF. 8 ml of methanol are slowly added dropwise, within 5 h and at 40° C., to this mixture. The end of the reaction is established by thin layer chromatography, and the reaction mixture is poured into 80 ml of a 10% solution of citric acid. The mixture is extracted 4 times with 30 ml of ethyl acetate on each occasion and the combined extracts are dried over MgSO$_4$. After evaporating off the solvent in vacuo and chromatographing the residue on 208 g of silica gel (dichloromethane:methanol 9:1), 3.37 g (64%) of the title compound are obtained.

EXAMPLE VII (2S)-2-[N$^G$-(4-Methyl-phenylsulphonyl)-S-arginyl-S-valinyl]amino-3-phenylpropan-1-ol dihydrochloride

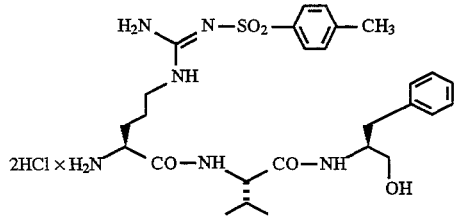

As described for Example I, 18.68 g (99% of theory) of the title compound are obtained as a colourless powder from 18.90 g (28.60 mmol) of the compound from Example VI.

M.p.: 161°–162° C. R$_f$=0.36 (acetonitrile:water 9:1) MS (FAB) m/z=561 (M+H)$^+$ IR (KBr) 2964, 1655, 1560, 1342, 1171, 1090, 1041, 666 cm$^{-1}$ [α]$^{20}$$_D$=2.3° (c=0.983, CH$_3$OH) $^1$H-NMR (250 MHz, DC$_3$OD): δ=0.96 (m, 6H, [CH$_3$]$_2$CH); 1.50 (m, 2H, CH$_2$); 1.80 (m, 2H, CH$_2$); 2.03 (m, 1H [CH$_3$]$_2$CH); 2.42 (s, 3H, CH$_3$); 2.68 (dd, J=8 Hz, 14 Hz, 1H, CH$_2$Ph); 2.86 (dd, J=6 Hz, 14 Hz, 1H, CH$_2$Ph); 3.12 (t, J=6.5 Hz, 2H, CH$_2$N); 3.51 (d, J=6 Hz, 2H, CH$_2$O); 3.97 (m, 1H, NCHCO-Arg); 4.07 (m, 1H, NCH); 4.18 (d, J=7.5 Hz, NCHCO-Val); 7.18 (m, 5H, Ph); 7.45, 7.87 (AB, J=10 Hz, 4H, H arom.) C$_{27}$H$_{40}$N$_6$O$_5$S×2 HCl (633.66) Calc.: C 51.18 B 6.68 N 13.26 Found: C 49.9 B 6.8 N 13.3

EXAMPLE VIII

Nα-(tert-Butoxycarbonyl)-N$^G$-(4-methyl-phenylsulphonyl)-S-arginyl-S-valinyl-S-phenylalanine methyl ester

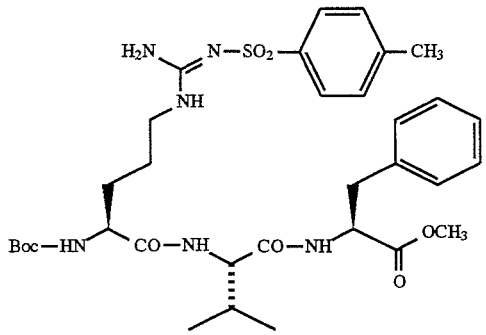

As described for Example VI (method A), 13.66 g (69% of theory) of the title compound are obtained as a colourless foam, after 3 h at room temperature, from 14.14 g (33.00 mmol) of N$_g$-(tert-butoxycarbonyl)-N$^G$-(4-methylphenylsulphonyl)-S-arginine and 9.02 g (28.70 mmol) of S-valinyl-S-phenylalanine methyl ester hydrochloride [EP 77 029; A. Orlowska et al. Pol. J. Chem. 54, 2329 (1980)].

R$_f$=0.33 (ethyl acetate) MS (FAB) m/z=689 (M+H)$^+$ IR (KBr) 3343, 2967, 1740, 1655, 1546, 1254, 1169, 1132, 1083, 676 cm$^{-1}$ [α]$^{20}$$_D$=–9.1° (c=0.389, DMSO) $^1$H-NMR (250 MHz, DMSO$_{d6}$/D$_2$O): δ=0.82 (m, 6H, [CH$_3$]$_2$CH); 1.49 (s, CH$_3$—C); 1.3–1.5 (m, CH$_2$) together 13H, 1.95 (m, 1H, [CH$_3$]$_2$CH); 2.35 (s. 3H, CH$_3$); 3.05 (m, 4H, CH$_2$Ph, CH$_2$N); 3.60 (s, 3H, COOCH$_3$); 3.89 (m, 1H, NCHCO); 4.49 (m, 1H, NCHCO); 7.15–7.30 (m, 5H, Ph); 7.33, 7.68 (AB, J=10 Hz, 4H, H arom.)

EXAMPLE IX

N$^G$-(4-Methyl-phenylsulphonyl)-S-arginyl-S-valinyl-S-phenylalanine methyl ester dihydrochloride

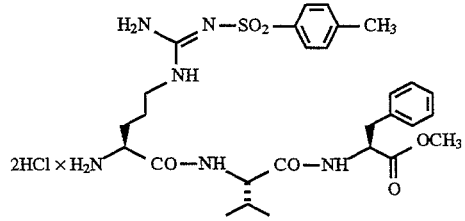

As described for Example I, 10.18 g (92% of theory) of the title compound are obtained as a colourless powder from 11.50 g (16.70 mmol) of the compound from Example VIII.

M.p.: from 190° C. (Decomp.)

R$_f$=0.18 (dichloromethane:methanol 9:1)

MS (FAB): m/z=589 (M+H)$^+$

IR (KBr) 2963, 1744, 1670, 1549, 1364, 1218, 1171, 1086, 668 cm$^{-1}$

[α]$^{20}$$_D$=7.6° (c=0.493, DMSO)

$^1$H-NMR (250 MHz, DMSO$_{d6}$/CD$_3$OD) δ=0.97 (d, J=8 Hz, 6H, [CH$_3$]$_2$CH); 1.41, 1.62 (m, 4H, CH$_2$); 2.00 (m, 1H,

[CH₃]₂CH); 2.35 (s, 3H, CH₃); 2.90–3.15 (m, 4H, CH₂Ph, CH₂N); 3.58 (s, 3H, COOCH₃); 3.86 (m, 1H, NHCHCO); 4.25 (m, NCHCO, below HDO); 4.52 (m, 1H, NCHCO); 7.22 (m, 5H, Ph); 7.30, 7.68 (AB, J=9 Hz, 4H, H arom).

Example X

Nα-(tert-Butoxycarbonyl)-N$^G$-(4-methyl-phenyl sulphonyl)-S-arginyl-S-valinyl-S-phenylalanine

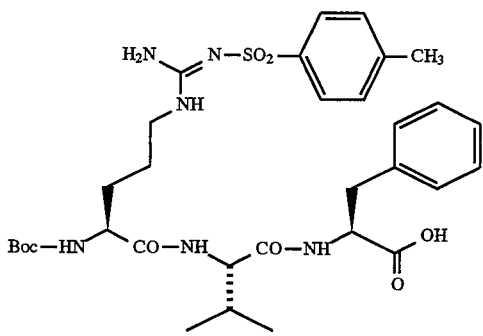

29 mg (0.70 mmol) of lithium hydroxide hydrate are added to a solution of 241 mg (0.35 mmol) of the compound from Example 3 in 2.6 ml of THF and 0.7 ml of water, and the mixture is then stirred at room temperature for 20 min. After this, the reaction mixture is poured into 30 ml of ethyl acetate. The organic phase is separated off, and the aqueous phase is extracted once again with 10 ml of ethyl acetate. The aqueous phase is freed of solvent residues in a rotary evaporator and adjusted to pH 5.2 with 0.5N hydrochloric acid. The resulting precipitate is thoroughly stirred for 10 min, separated off by filtration, and dried under high vacuum, initially over KOH and then over Sicapent. 175 mg (74%) of the title compound are obtained as an amorphous powder.

M.p.: 139° C. (Decomp.)
$R_f$=0.36 (acetonitrile:water=9:1)
MS (FAB) m/z=675 (M+H)⁺

PREPARATION EXAMPLES

The compounds described in Table I are obtained, as described for Example VI (method A), by condensing the amines from Table II with different protected amino acids:

Example 4

(2S)-[Nα-(tert-Butoxycarbonyl)-N$^g$-(4-methyl-phenylsulphonyl)-S-arginyl-(S)-N-methyl-valinyl] amino-S-phenylpropan-1-ol

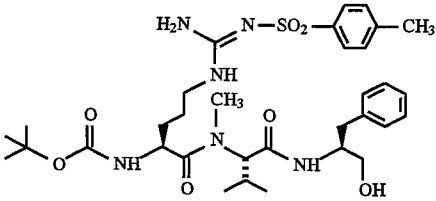

517 mg (2.03 mmol) of bis-(2-oxo-3-oxazolidinyl)-phosphoryl chloride are added to a suspension, which is stirred and cooled down to −10° C., of 555 mg (1.85 mmol) of the compound from Example V and 793 mg (1.85 mmol) of Nα-(tert-butoxycarbonyl)-N$^G$-(4-methylphenylsulphonyl)-S-arginine in 10 ml of anhydrous dichloromethane, whereupon a clear solution is produced. After this, 1.14 ml (6.53 mmol) of ethyl-diisopropylamine are added, and the reaction mixture is then stirred at −10° C. for 2 h and subsequently poured into 55 ml of 1N NaHCO₃ solution. The organic phase is separated off and the water phase is extracted with 20 ml of dichloromethane. The combined organic extracts are washed with 50 ml of water and dried over MgSO₄. After the solvent has been evaporated off in vacuo and the residue has been chromatographed on 35 g of silica gel (dichloromethane:methanol 95:5), 474 mg (38%) of the title compound are obtained as a pale foam.

$R_f$=0.35 (dichloromethane:methanol 9:1)

MS (FAB): m/z=675 (M+H)⁺, 1349 (2M+H)⁺

The products listed in Table 2 are obtained, as described for Example 4, by coupling the compounds from Table II with the corresponding protected arginine derivatives in the presence of bis-(2-oxo-3-oxazolidinyl)-phosphoryl chloride:

TABLE 1

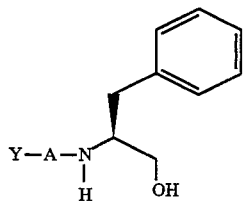

| Ex. No. | Y | A | Yield (% of theory) | MS (FAB) m/z(M + H)⁺ | $R_f$/eluent ratio | M.p. (°C.) |
|---|---|---|---|---|---|---|
| 1 | Boc—Lys(Tos)— | —Val— | 68 | 633 | 0.31, I (9:1) | Foam |
| 2 | Z—Lys(Z)— | —Val— | 66 | 647 | 0.35, I (9:1) | 178 |
| 3 | Z—Orn(Z)— | —Val— | 45 | 633 | 0.45, I (9:1) | 176 |

TABLE 2

Y—A—N(H)—CH(CH2Ph)—CH2OH [structure with phenyl and OH]

| Ex. No. | Y | A | Yield (% of theory) | MS (FAB) m/z(M + H)⁺ | R$_f$/eluent ratio | M.p. (°C.) |
|---|---|---|---|---|---|---|
| 5 | Z—Arg(Tos)— | —N—CH$_3$—Val— | 67 | 709 | 0.48, I (9:1) | Foam |
| 6 | Boc—Arg(NO$_2$)— | —Val— | 22 | 552 | 0.28, I (9:1) | 122 |

The dihydrochlorides described in Table 3 are obtained, in analogy with Example VII, by eliminating the tert-butoxycarbonyl group from the compound of Example 4:

TABLE 3

2 HCl × H—Y—A—N(H)—CH(CH2Ph)—CH2OH

| Ex. No. | Y | A | Yield (% of theory) | MS (FAB) m/z(M + H)⁺ | R$_f$/eluent ratio | M.p. (°C.) |
|---|---|---|---|---|---|---|
| 7 | Arg(Tos)— | —N—CH$_3$—Val— | 86 | 575 | 0.17, I (85:15) | 158 |

Example 8

(2S)-2-[N$_\alpha$-(tert-Butyl)acetyl-N$^G$-(4-methylphenylsulphonyl)-S-arginyl-S-valinyl]amino-3-phenyl-propan-1-ol

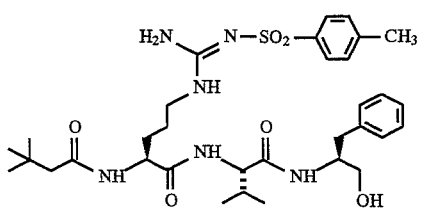

139 μl (1.00 mmol) of 3,3-dimethylbutyryl chloride are added dropwise to a solution, which is cooled to 0° C., of 634 mg (1.00 mmol) of the compound from Example IX in 20 ml of anhydrous dichloromethane and 385 μl (3.50 mmol) of N-methylmorpholine. After 15 min at 0° C., the mixture is stirred into 50 ml of cold NaHCO$_3$ solution. The organic phase is separated off, the water phase is extracted with 10 ml of dichloromethane, and the combined organic extracts are dried over MgSO$_4$. Following chromatography on 40 g of silica gel (dichloromethane:methanol 9:1) and crystallization of the product from 50 ml of ether, 370 mg (55%) of the title compound are obtained as colourless crystals.

M.p.: from 124° C. (Decomp.)

R$_f$=0.55 (dichloromethane:methanol 85:15)

MS (FAB) m/z=659 (M+H)⁺

Example 9

(2S)-2-[N$_\alpha$-(4-Methyl-phenylsulphonyl)-N$^G$-(4-methylpropenyl sulphonyl)-S-arginyl-S-valinyl]amino-3-phenylpropan-1-ol

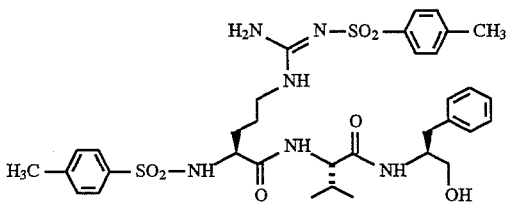

As described for Example 8, 1.13 g (63%) of the title compound are obtained as colourless crystals by reacting 1.59 g (2.50 mmol) of the compound from Example V with 0.53 g (2.75 mmol) of 4-methylphenylsulphonyl chloride in the presence of 1.05 ml (7.50 mmol) of triethylamine in 20 ml of anhydrous dichloromethane, after 1 h at room temperature and chromatography of the crude product on 65 g of silica gel (dichloromethane:methanol 95:5).

M.p.: 124°–126° C.

R$_f$=0.60 (dichloromethane:methanol 85:15)

MS (FAB) m/z=715 M+H)⁺

Example 10

(2S)-2-[N_α-Quinoline-2-carbonyl-N^G-(4-methyl-phenylsulphonyl)-S-arginyl-S-valinyl]amino-3-phenyl-propan-1-ol

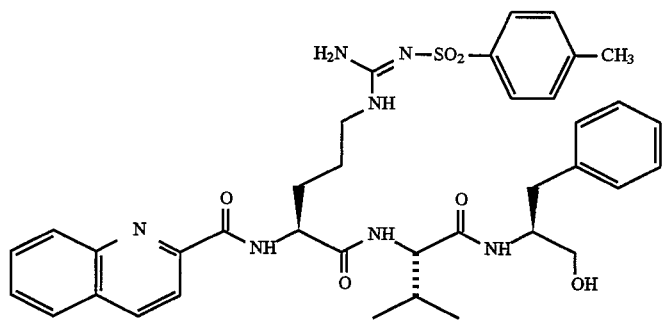

430 mg (2.10 mmol) of DCC are added to a solution, which is cooled to 0° C. and stirred, of 381 mg (2.20 mmol) of quinoline-2-carboxylic acid and 337 mg (2.20 mmol) of HOBT in 30 ml of anhydrous dichloromethane, and the mixture is then stirred for 5 min. After this, a solution of 1.27 g (2.00 mmol) of the compound from Example VII and 0.77 ml (7.00 mmol) of N-methylmorpholine in 30 ml of dichloromethane is added dropwise. The cooling bath is removed and the reaction mixture is left stirring at room temperature for 2 h. The end of the reaction is established by thin layer chromatography. The resulting urea is separated off by filtration, the filtrate is concentrated in vacuo, and the crude product is purified by chromatography on 92 g of silica gel (dichloromethane:methanol 95:5). 603 mg (44% of theory) of the title compound are obtained as colourless crystals.

M.p.: 100° C.

$R_f$=0.29 (dichloromethane:methanol 9:1)

MS (FAB) m/z=716 (M+H)⁺

The products listed in Table 4 are obtained, as described for Example 10, by condensing the compound from Example VII with the corresponding acids:

TABLE 4

| Ex. No. | Y | Yield (% of theory) | MS (FAB) m/z(M + H)⁺ | $R_f$/eluent ratio | M.p. (decomp.) (°C.) |
|---|---|---|---|---|---|
| 11 | naphthyl-CH₂-C(O)- | 52 | 729 | 0.37, I (9:1) | 127 |
| 12 | biphenyl-CH₂-C(O)- | 56 | 755 | 0.30, I (9:1) | 147 |

TABLE 4-continued

| Ex. No. | Y | Yield (% of theory) | MS (FAB) m/z(M + H)⁺ | R_f/eluent ratio | M.p. (decomp.) (°C.) |
|---|---|---|---|---|---|
| 13 | 2-acetyl-1H-indole | 62 | 704 | 0.25, I (9:1) | 138 |
| 14 | (4-fluorophenyl)acetone | 52 | 697 | 0.31, I (9:1) | 101 |
| 15 | (4-trifluoromethylphenyl)acetone | 58 | 747 | 0.27, I (9:1) | 155 |
| 16 | (4-methoxyphenyl)acetone | 72 | 709 | 0.38, I (9:1) | 150 |
| 17 | (4-hydroxyphenyl)acetone | 51 | 695 | 0.23, I (9:1) | 100 |
| 18 | [4-(1H-1,2,3-triazol-1-yl)phenyl]acetone | 58 | 746 | 0.28, I (9:1) | 133 |
| 19 | [4-(4-phenyl-2H-1,2,3-triazol-2-yl)phenyl]acetone | 86 | 822 | 0.26, I (9:1) | 153 |
| 20 | (2,4-difluorophenoxy)acetone | 47 | 731 | 0.16, I (9:1) | 109 |

TABLE 4-continued

| Ex. No. | Y | Yield (% of theory) | MS (FAB) m/z(M + H)+ | R$_f$/eluent ratio | M.p. (decomp.) (°C.) |
|---|---|---|---|---|---|
| 21 | 1,1-diphenylacetone group | 57 | 755 | 0.64, I (9:1) | 138 |
| 22 | 2-acetylpyrazine group | 53 | 667 | 0.25, I (9:1) | 129 |
| 23 | bis(naphthylmethyl)acetone group | 22 | 883 | 0.28, I (9:1) | 130 |
| 24 | 2-acetylquinoxaline group | 35 | 717 | 0.31, I (9:1) | 116 |
| 25 | acetophenone group | 98 | 665 | 0.30, I (9:1) | 108 |
| 26 | phenylacetone group | 97 | 679 | 0.30, I (9:1) | 100 |

TABLE 4-continued

[Structure: Tosyl-guanidino-arginine-valine-phenylalaninol tripeptide with Y-NH group, where the core structure shows H₂N-C(=N-SO₂-C₆H₄-CH₃)-NH-(CH₂)₃-CH(NHY)-C(=O)-NH-CH(iPr)-C(=O)-NH-CH(CH₂Ph)-CH₂OH]

| Ex. No. | Y | Yield (% of theory) | MS (FAB) m/z(M + H)⁺ | R$_f$/eluent ratio | M.p. (decomp.) (°C.) |
|---|---|---|---|---|---|
| 27 | 3-pyridyl-CH₂-C(=O)-CH₂- | 14 | 680 | 0.23, I (9:1) | 128 |
| 28 | 4-methoxyphenyl-CH₂CH₂-C(=O)-CH₂- | 65 | 723 | 0.27, I (9:1) | 140 |
| 29 | 2-nitrophenyl-CH₂CH₂-C(=O)-CH₂- | 39 | 738 | 0.20, I (9:1) | 108 |
| 30 | 4-pyridyl-S-CH₂-C(=O)-CH₂- | 33 | 712 | 0.15, I (9:1) | 152 |
| 31 | quinolin-8-yl-CH₂-C(=O)-CH₂- | 42 | 730 | 0.19, I (9:1) | 112 |

Example 32

(2S)-2-[N$_\alpha$-(2,6-Dichloro-phenyl-methoxycarbonyl)-N$^G$-(4-methyl-phenylsulphonyl)-S-arginyl-S-valinyl] amino-3-phenyl-propan-1-ol

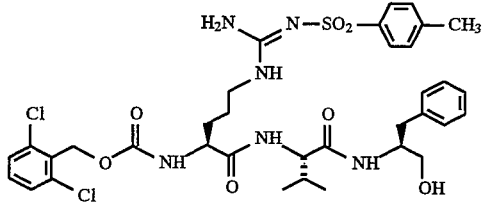

551 mg (2.30 mmol) of 2,6-dichloro-benzyloxycarbonyl chloride are added in portions, within the space of 2 h, to a solution, which is cooled to 0° C. and stirred, of 1.27 g (2.00 mmol) of the compound from Example VII in 9 ml of dioxane and 6 ml of water, a pH of 9–10 being maintained during this procedure by the concomitant addition of a 2N aqueous solution of NaOH. After this, the mixture is stirred into a mixture of 15 ml of ice water, 6 ml of 1N citric acid and 30 ml of ethyl acetate. The organic phase is separated off and the water phase is extracted 5 times with 20 ml of ethyl acetate on each occasion. The combined organic extracts are dried over MgSO$_4$. After evaporating off the solvent in vacuo and chromatographing the residue on 84 g of silica gel (dichloromethane:methanol 95:5), and crystallizing the product from 50 ml of ether, 1.08 g (71%) of the title compound are obtained as colourless crystals.

M.p.: from 144° C. (Decomp.)
R$_f$=0.34 (dichloromethane:methanol 9:1)
MS (FAB) m/z=763 (M+H)$^+$ The compounds listed in Table 5 are obtained, as described for Example 32, by reacting the compound from Example VII with the corresponding benzyloxycarbonyl chlorides:

Example 35

(2S)-2-[N$_\alpha$-(2,4-Dimethyl-benzyloxycarbonyl)-N$^G$-(4-methylphenylsulphonyl)-S-arginyl-S-valinyl] amino-3-phenyl-propan-1-ol

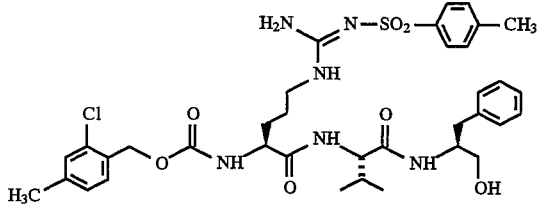

A stirred suspension of 634 mg (1.00 mmol) of the compound from Example VII and 331 mg (1.10 mmol) of 4-nitrophenyl-2,4-dimethylphenyl-methyl [prepared in accordance with D.F. Veber et al., J. Org. Chem. 42, 3286 (1977)] in 5 ml of dioxane and 5 ml of water is maintained at pH 7.5 by the continuous addition of an aqueous 2N solution of NaOH (requirement about 1.1 ml), and stirred at room temperature for 21 h. The end of the reaction is established by thin layer chromatography, and the reaction mixture is then stirred into a mixture consisting of 20 ml of 1N citric acid and 15 ml of ethyl acetate. The aqueous phase is separated off, adjusted to pH 9 by adding 2N NaOH, and extracted twice with 15 ml of ethyl acetate on each occasion. The combined organic extracts are dried over MgSO$_4$. The solvent is evaporated off in vacuo and the residue is purified by chromatography on 47 g of silica gel (dichloromethane:methanol 95:5). The product fractions are crystallized from dichloromethane/ether. 339 mg (47%) of the title compound are obtained as colourless crystals.

M.p.: from 121° C. (Decomp.)
R$_f$=0.26 (dichloromethane:methanol 9:1)
MS (FAB) m/z=723 (M+H)$^+$ The compounds listed in Table 6 are obtained, as described for Example 35, by reacting the compound from Example VII with the corresponding 4-nitrophenyl carbonates:

TABLE 5

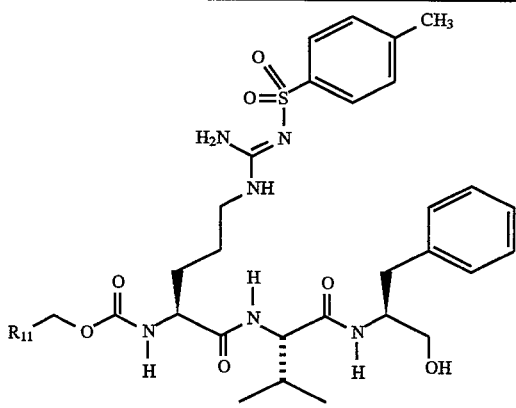

| Ex. No. | R$^{11}$ | Yield (% of theory) | MS (FAB) m/z(M + H)$^+$ | R$_f$/eluent ratio | M.p. (decomp.) (°C.) |
|---|---|---|---|---|---|
| 33 | 4-NO$_2$—C$_6$H$_4$— | 72 | 740 | 0.31,I (9:1) | 116 |
| 34 | 2-NO$_2$—,4,5-CH$_3$O—C$_5$H$_2$— | 66 | 800 | 0.38,I (9:1) | 176 |

TABLE 6
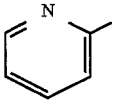
| Ex. No. | R{11} | Yield (% of theory) | MS (FAB) m/z(M + H)+ | R{f}/eluent ratio | M.p. (decomp.) (°C.) |
|---|---|---|---|---|---|
| 36 | 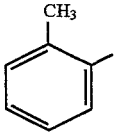 2-pyridyl | 40 | 696 | 0.40,I (85:15) | 112 |
| 37 | 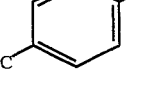 2-CH3-phenyl | 58 | 709 | 0.32,I (9:1) | 117 |
| 38 | 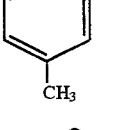 4-CH3-phenyl | 62 | 709 | 0.29,I (9:1) | 98 |
| 39 | 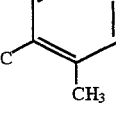 3-CH3-phenyl | 60 | 709 | 0.30,I (9:1) | 106 |
| 40 | 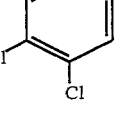 3,4-di-CH3-phenyl | 53 | 723 | 0.22,I (9:1) | 142 |
| 41 | 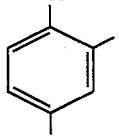 3,4-di-Cl-phenyl | 38 | 763 | 0.34,I (9:1) | 108 |
| 42 | 2,4-di-Cl-phenyl | 51 | 763 | 0.29,I (9:1) | 110 |
| 43 | 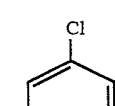 2,4-di-Cl-phenyl | 56 | 763 | 0.34,I (9:1) | 119 |

TABLE 6-continued

[Structure shown: tosyl-guanidino arginyl-valinyl-phenylalaninol derivative with R₁₁-O-C(=O)-NH- group]

| Ex. No. | R₁₁ | Yield (% of theory) | MS (FAB) m/z(M + H)⁺ | R_f/eluent ratio | M.p. (decomp.) (°C.) |
|---|---|---|---|---|---|
| 44 | H₃CO-C₆H₄-CH₃ (4-methoxybenzyl type) | 57 | 725 | 0.36, I (9:1) | 109 |
| 44a | 2-pyridylmethyl | 22 | 710 | 0.21, I (9:1) | Foam |

Example 45

(2R,S)-2-[N_α-(Benzyloxycarbonyl)-N^G-(4-methyl-phenylsulphonyl)-S-arginyl-S-valinyl]amino-3-phenyl-propan-1-al

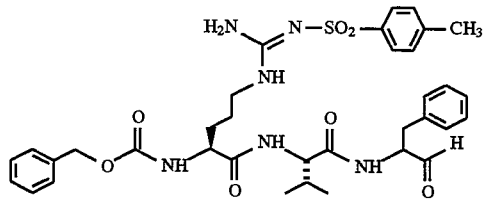

804 mg (5.05 mmol) of pyridine sulphur trioxide complex are added to a solution of 780 mg (1.12 mmol) of the compound from Example 26 in 8 ml of anhydrous DMSO and 1.14 ml (10.10 mmol) of triethylamine, and the mixture is then stirred at room temperature for 1 h. After this, the reaction mixture is stirred into 20 ml of ether. The mixture is left to stand for a short while during which an oil separates out. The ether phase is decanted off and the oil is taken up in 5 ml of toluene. The toluene is evaporated off in vacuo, and the residue is chromatographed on 80 g of silica gel (dichloromethane:methanol 95:5). 500 mg (65%) of the title compound are obtained as a colourless oil (diastereomeric mixture).

$R_f$=0.44, 0.52 (dichloromethane:methanol 9:1)

MS (FAB): m/z=693 (M+H)⁺

The compounds listed in Tables 7 and 8 are obtained, as described for Example 45, by oxidizing the alcohols:

TABLE 7

[Structure: Y-A-NH-CH(CH₂Ph)-CHO]

| Ex. No. | Y— | A— | Yield (% of theory) | MS (FAB) m/z(M + H)⁺ | R_f/eluent ratio | M.p. (decomp.) (°C.) |
|---|---|---|---|---|---|---|
| 46 | Boc—Lys(Tos)— | Val— | 87 | 631 | 0.43,0.49,I (9:1) | Foam |
| 47 | Z—Lys(Z)— | Val— | 69 | 645 | 0.39,0.44,I (9:1) | 138 |
| 48 | Z—Orn(Z)— | Val— | 45 | 631 | 0.47,0.49,I (9:1) | 135 |
| 49 | Boc—Arg(Tos)— | NCH₃Val— | 55 | 673 | 0.50, I (9:1) | Foam |

TABLE 7-continued

Y—A—NH—CH(CH2Ph)—CHO

| Ex. No. | Y— | A— | Yield (% of theory) | MS (FAB) m/z(M + H)+ | Rf/eluent ratio | M.p. (decomp.) (°C.) |
|---|---|---|---|---|---|---|
| 50 | Z—Arg(Tos)— | NCH3Val— | 62 | 707 | 0.23, I (9:1) | Foam |
| 51 | Boc—Arg(NO2) | Val— | 62 | 550 | 0.21,0.25,I (9:1) | 114 |

TABLE 8

R1-NH-CH(CH2CH2CH2NH-C(=NH)-NH-SO2-C6H4-CH3)-CO-NH-CH(iPr)-CO-NH-CH(CH2Ph)-CHO

| Ex. No. | R1 | Yield (% of theory) | MS (FAB) m/z(M + H)+ | Rf/eluent ratio | M.p. (decomp.) (°C.) |
|---|---|---|---|---|---|
| 52 | (CH3)3C-CH2-CO-CH2-CO- | 46 | 657 | 0.24,0.27,I(9:1) | 109 (decomp.) |
| 53 | quinolin-2-yl-CO- | 90 | 714 | 0.34,0.38,I(9:1) | Foam |
| 54 | indol-2-yl-CO- | 45 | 702 | 0.29,0.32,I(9:1) | 124 (decomp.) |
| 55 | 4-F-C6H4-CH2-CO- | 70 | 695 | 0.28,0.34,I(9:1) | 120 (decomp.) |
| 56 | 4-CF3-C6H4-CH2-CO- | 68 | 745 | 0.22,0.25,I(9:1) | 108 (decomp.) |
| 57 | 4-CH3O-C6H4-CH2-CO- | 65 | 707 | 0.35,0.42,I(9:1) | 100 (decomp.) |

TABLE 8-continued
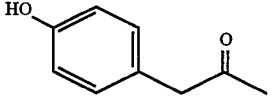
| Ex. No. | R¹ | Yield (% of theory) | MS (FAB) m/z(M + H)⁺ | R$_f$/eluent ratio | M.p. (decomp.) (°C.) |
|---|---|---|---|---|---|
| 58 | 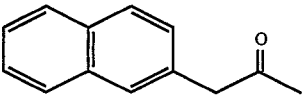 | 60 | 693 | 0.21,0.25,I(9:1) | 117 (decomp.) |
| 59 | 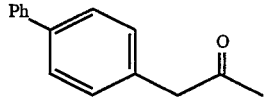 | 81 | 727 | 0.31,0.35,I(9:1) | oil |
| 60 | 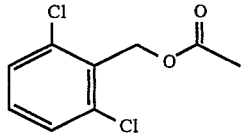 | 90 | 753 | 0.36,0.41,I(9:1) | oil |
| 61 | 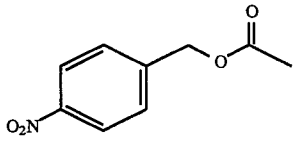 | 90 | 761 | 0.28,0.34,I(9:1) | oil |
| 62 | 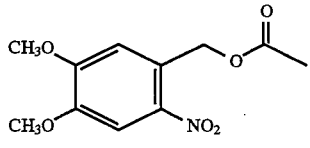 | 60 | 738 | 0.25,0.33,I(9:1) | oil |
| 63 | 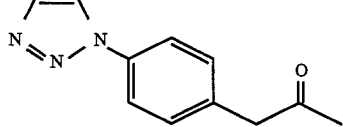 | 39 | 798 | 0.31,0.36,I(9:1) | 109 (decomp.) |
| 64 | 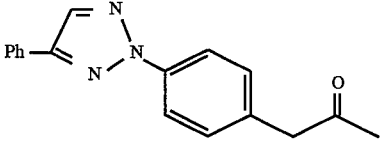 | 64 | 744 | 0.23,0.29,I(9:1) | 110 (decomp.) |
| 65 |  | 46 | 820 | 0.42,0.50,I(9:1) | 124 (decomp.) |

TABLE 8-continued

[Structure shown: R₁-NH-CH(CH₂CH₂CH₂-NH-C(=NH)-NH-SO₂-C₆H₄-CH₃)-C(=O)-NH-CH(CH(CH₃)₂)-C(=O)-NH-CH(CH₂-C₆H₅)-CHO, with H₂N on the guanidine]

| Ex. No. | R¹ | Yield (% of theory) | MS (FAB) m/z(M + H)⁺ | $R_f$/eluent ratio | M.p. (decomp.) (°C.) |
|---|---|---|---|---|---|
| 66 | 2,4-difluorophenoxy-CH₂-C(=O)- | 72 | 729 | 0.33,0.40,I(9:1) | 86 |
| 67 | Ph₂CH-C(=O)-CH₃ | 49 | 753 | 0.44,0.50,I(9:1) | 125 |
| 68 | 2×HCl× pyrazinyl-C(=O)-CH₃ | 48 | 665 | 0.37,0.42,I(9:1) | amorphous |
| 69 | H₃C-C₆H₄-SO₂- | 88 | 713 | 0.41,0.44,I(9:1) | 96 |
| 70 | pyridin-2-yl-CH₂-O-C(=O)-CH₃ | 62 | 694 | 0.31,0.35,I(9:1) | 103 |
| 71 | 2-CH₃-C₆H₄-CH₂-O-C(=O)-CH₃ | 63 | 707 | 0.33,0.39,I(9:1) | foam |
| 72 | 4-CH₃-C₆H₄-CH₂-O-C(=O)-CH₃ | 89 | 707 | 0.34,0.37,I(9:1) | foam |
| 73 | 3-CH₃-C₆H₄-CH₂-O-C(=O)-CH₃ | 54 | 707 | 0.30,0.34,I(9:1) | 105 |

TABLE 8-continued
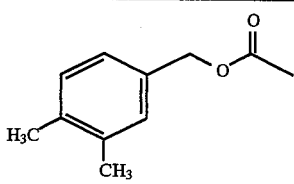
| Ex. No. | R¹ | Yield (% of theory) | MS (FAB) m/z(M + H)⁺ | $R_f$/eluent ratio | M.p. (decomp.) (°C.) |
|---|---|---|---|---|---|
| 74 | 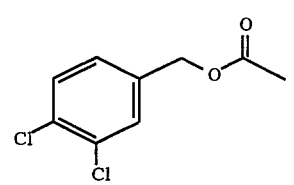 | 84 | 721 | 0.35,0.38,I(9:1) | foam |
| 75 | 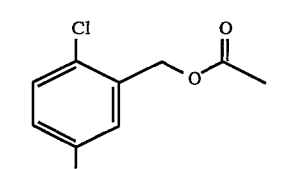 | 50 | 761 | 0.40,0.44,I(9:1) | 95 |
| 76 | 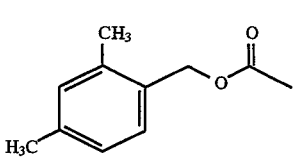 | 22 | 761 | 0.42,0.45,I(9:1) | foam |
| 77 | 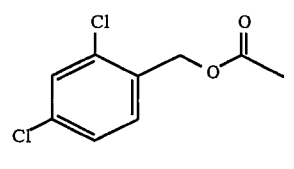 | 71 | 721 | 0.36,0.39,I(9:1) | 95 |
| 78 | 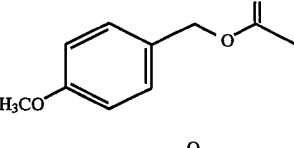 | 72 | 761 | 0.23,0.31,I(9:1) | 98 |
| 79 | 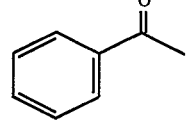 | 88 | 723 | 0.44,0.48,I(9:1) | foam |
| 80 |  | 63 | 663 | 0.28,0.31,I(9:1) | 99 |

TABLE 8-continued

| Ex. No. | R¹ | Yield (% of theory) | MS (FAB) m/z(M + H)⁺ | R_f/eluent ratio | M.p. (decomp.) (°C.) |
|---|---|---|---|---|---|
| 81 | (phenyl-CH₂-C(O)-) | 57 | 677 | 0.31,0.35,I(9:1) | 102 |
| 82 | (quinoxalin-2-yl-C(O)-) | 58 | 715 | 0.34,0.39,I(9:1) | 122 |
| 83 | 2×HCl× (pyridin-3-yl-CH₂-C(O)-) | 67 | 678 | 0.30,0.38,I(9:1) | foam |
| 84 | (4-methoxyphenyl-CH₂CH₂-C(O)-) | 79 | 721 | 0.26,0.30,I(9:1) | 104 |
| 85 | (2-nitrophenyl-CH₂CH₂-C(O)-) | 72 | 736 | 0.44,0.48,I(9:1) | 102 |
| 86 | 2HCl× (pyridin-4-yl-S-CH₂-C(O)-) | 53 | 710 | 0.26,0.30,I(9:1) | foam |
| 87 | 2HCl× (quinolin-8-yl-CH₂-C(O)-) | 41 | 728 | 0.49,0.53,I(9:1) | foam |
| 88 | 2HCl× (pyridin-2-yl-CH₂CH₂-O-C(O)-) | 46 | 708 | 0.40,0.42,I(9:1) | foam |

We claim:

1. A valine-containing, substituted pseudopeptide of the formula

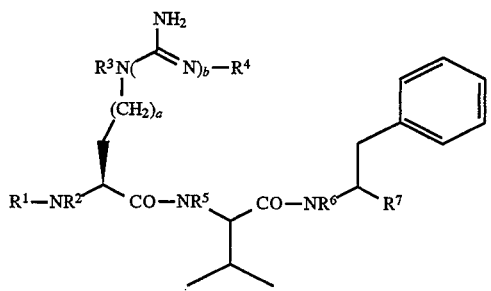

in which a represents a number 2 or 3, b represents a number 0 or 1, $R^1$ represents hydrogen, or represents a radical of the formula $R^8-NR^9-CO-$, $R^{10}-(CH_2)_c-CO-$, $R^{11}-(CH_2)_d-O-CO$, or represents a radical of the formula $-SO_2-R^{12}$, in which $R^8$ denotes cycloalkyl having 3 to 6 carbon atoms; or denotes optionally substituted straight-chain or branched alkyl having up to 18 carbon atoms wherein the substituents are hydroxyl, straight-chain or branched alkoxy having up to 4 carbon atoms, halogen, trifluoromethyl, trifluoromethoxy, cycloalkyl having 3 to 6 carbon atoms, aryl having 6 to 10 carbon atoms which is optionally substituted identically or differently up to two times wherein the substituents are carboxyl, cyano, hydroxyl, halogen, $C_1-C_5$ perhalogenoalkyl straight-chain or branched $C_1-C_6$ acyl, straight-chain or branched $C_1-C_6$ alkoxy, straight-chain or branched $C_1-C_6$ alkoxycarbonyl or alkyl which is optionally substituted by a group of the formula $-CO_2R^{13}$ in which $R^{13}$ denotes hydrogen, or straight-chain or branched alkyl or alkenyl having in each case up to 8 carbon atoms which are optionally substituted by phenyl, or $R^8$ denotes aryl having 6 to 10 carbon atoms which is optionally substituted identical or differently up to three times by carboxyl, amino, halogen, hydroxyl, cyano, $C_1-C_5$ perhalogenoalkyl straight-chain or branched $C_1-C_6$ acyl, straight-chain or branched $C_1-C_6$ alkoxy, vinyl-$C_1-C_6$-alkoxycarbonyl, straight-chain or branched alkoxycarbonyl, or denotes an amino acid radical of the formula,

in which $R^{14}$ and $R^{15}$ are identical or different and denote hydrogen or methyl, or $R^{14}$ and $R^{15}$ together form a 5- or 6-membered saturated carbocyclic ring, or $R^{14}$ denotes hydrogen or methyl, and $R^{15}$ denotes cycloalkyl having 3 to 8 carbon atoms, aryl having 6 to 10 carbon atoms, or hydrogen; or denotes straight-chain or branched alkyl having up to 8 carbon atoms, where the alkyl is optionally substituted by methylthio, hydroxyl, mercapto, guanidyl, or by a group of the formula $-NR^{17}R^{18}$ or $R^{19}-OC-$, in which $R^{17}$ and $R^{18}$, independently of each other, denote hydrogen, straight-chain or branched alkyl having up to 8 carbon atoms, or phenyl, and $R^{19}$ denotes hydroxyl, benzyloxy, alkoxy having up to 6 carbon atoms, or the above-listed group $-NR^{17}R^{18}$, $R^{16}$ denotes straight-chain or branched alkyl having up to 8 carbon atoms which is optionally substituted by hydroxyl or by straight-chain or branched alkoxy having up to 6 carbon atoms; or denotes carboxyl, allyloxycarbonyl, straight-chain or branched alkoxycarbonyl having up to 8 carbon atoms, or benzyloxycarbonyl;

or the alkyl is optionally substituted by cycloalkyl having 3 to 8 carbon atoms or by optionally substituted aryl having 6 to 10 carbon atoms wherein the substituents are hydroxyl, halogen, nitro, $C_1-C_8$ alkoxy or by the group $-NR^{17}R^{18}$, in which $R^{17}$ and $R^{18}$ have the abovementioned meanings;

or the alkyl group is optionally substituted by a 5- to 6-membered nitrogen-containing heterocycle or indolyl in which the corresponding $-NH-$functions are optionally protected by alkyl having up to 6 carbon atoms by an amino protecting group, or $R^8$ denotes a radical of the formula

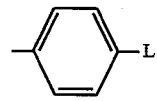

in which

L denotes phenyl or pyridyl, $R^9$ denotes hydrogen, straight-chain or branched alkyl having up to 6 carbon atoms, or an amino protecting group, $R^{10}$ denotes straight-chain or branched alkyl having up to 8 carbon atoms, $C_6-C_{10}$-aryloxy, $C_6-C_{10}$ aryl, indolyl, quinolyl, quinoxalinyl, isoquinolyl or a 5- to 7-membered, saturated or unsaturated heterocycle having up to 3 heteroatoms selected from the group consisting of S, N or O, wherein said aryloxy, aryl and heterocyclic rings are optionally substituted identically or differently up to 3 times by carboxyl, cyano, hydroxyl, halogen, amino, nitro, methylamino, $C_1-C_5$ perhalogenoalkyl, straight-chain or branched $C_1-C_6$ alkyl, straight-chain or branched $C_1-C_5$ acyl, straight-chain or branched $C_1-C_6$ alkoxy or straight-chain or branched $C_1-C_6$ alkoxycarbonyl, and additionally said aryl group is also optionally substituted by an optionally phenyl substituted 5- to 7-membered, saturated or unsaturated heterocycle having up to 3 heteroatoms selected from the group consisting of S, N or O, or $R^{10}$ denotes a radical of the formula

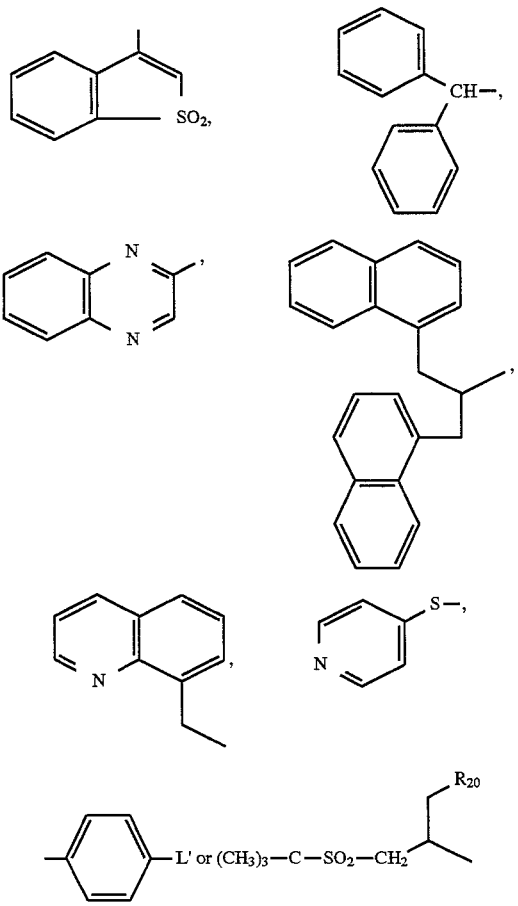

in which

L' has the abovementioned meaning of L and is identical to our different from the latter, $R^{20}$ denotes phenyl or naphthyl, c denotes a number 0, 1, 2 or 3, d denotes a number 0, 1, 2 or 3, $R^{11}$ has the abovementioned meaning of $R^{10}$ and is identical to or different from the latter, $R^{12}$ denotes methyl, phenyl or naphthyl which is optionally substituted identically or differently up to 4 times by methyl or methoxy; or denotes a radical of the formula

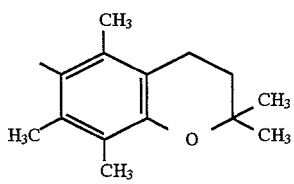

$R^2$, $R^3$, $R^5$ and $R^6$ are identical or different and represent hydrogen, straight-chain or branched alkyl having up to 4 carbon atoms, or represent an amino protecting group, $R^4$ represents nitro, an amino protecting group, or radical of the formula $—SO_2R^{21}$, in which $R^{21}$ has the abovementioned meaning of $R^{12}$ and is identical to or different from the latter, $R^7$ represents formyl or carboxyl, or represents straight-chain or branched alkoxycarbonyl having up to 8 carbon atoms, or represents a radical of the formula $—CH_2—OR^{22}$ or $—CH(OR^{23})_2$, in which $R^{22}$ and $R^{23}$ are identical or different and denote hydrogen, straight-chain or branched alkyl having up to 6 carbon atoms, or a hydroxyl protecting group, wherein said hydroxyl protecting group is selected from the group consisting of tert-butoxydiphenylsily, trimethylsilyl, triethylsilyl, triisopropylsilyl, tert-butyldimethylsilyl, tert-butyldiphenylsilyl, triphenylsilyl, trimethylsilylethoxycarbonyl, benzyl, benzyloxycarbonyl, 2-nitrobenzyl, 4-nitrobenzyl, 2-nitrobenzyloxycarbonyl, 4-nitrobenzyloxycarbonyl, tert-butyloxycarbonyl, allyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methylthiomethyl, methoxyethoxymethyl, [2-(trimethylsilyl)ethoxy]methyl, 2-(methylthiomethoxy)ethoxycarbonyl, benzoyl, 4-methylbenzoyl, 4-nitrobenzoyl, 4-fluorobenzoyl, 4-chlorobenzoyl or 4-methoxybenzoyl or a salt thereof, and wherein said amino protecting groups are selected from the group consisting of benzyloxycarbonyl 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxybenzyloxycarbonyl, cyclohexyloxycarbonyl, 1,1-dimethylethoxycarbonyl, adamantylcarbonyl, phthaloyl, 2,2,2-trichloroethoxycarbonyl, 2,2,2-trichloro-tert-butoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl, or benzyloxymethylene, 4-nitrobenzyl, 2,4-dinitrobenzyl or 4-nitrophenyl.

with the proviso that if a represents the number 2, b represents the number 1 and $R^5$ represents hydrogen, $R^1$ may not denote the radical of the formula $R^8—NH—CO—$.

2. A compound according to claim 1, in which a represents a number 2 or 3, b represents a number 0 or 1, $R^1$ represents hydrogen, or represents a radical of the formula $R^8—NR^9—CO—$, $R^{10}—(CH_2)_c—CO—$, $R^{11}—(CH_2)_d—O—CO$ or represents a radical of the formula $—SO_2—R^{12}$, in which $R^8$ denotes cyclopentyl or cyclohexyl; or denotes optionally substituted straight-chain or branched alkyl having up to 16 carbon atoms wherein the substituents are hydroxyl, methoxy, fluorine, chlorine, bromine, trifluoromethyl, trifluoromethoxy, cyclopentyl, cyclohexyl, phenyl which is optionally substituted identically or differently up to 2 times wherein the substituents are carboxyl, cyano, hydroxyl, fluorine, chlorine, bromine, $C_1$-$C_4$ perhalogenoalkyl, straight-chain or branched $C_1$-$C_4$-acyl, straight-chain or branched $C_1$-$C_4$ alkoxy, straight-chain or branched $C_1$-$C_4$ alkoxycarbonyl or alkyl which is optionally substituted by a group of the formula —$CO_2R^{13}$, in which $R^{13}$ denotes hydrogen, or straight-chain or branched alkyl or alkenyl having in each case up to 6 carbon atoms which are optionally substituted by phenyl, or $R^8$ denotes phenyl or naphthyl which is optionally substituted identically or differently up to 3 times by carboxyl, amino, fluorine, chlorine, bromine, hydroxyl, cyano, $C_1$-$C_4$ perhalogenoalkyl straight-chain or branched $C_1$-$C_5$ acyl, straight-chain or branched $C_1$-$C_5$ alkoxy, vinyl-$C_1$-$C_6$-alkoxycarbonyl, or straight-chain or branched $C_1$-$C_5$ alkoxycarbonyl, or denotes an amino acid radical of the formula,

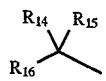

in which $R^{14}$ and $R^{15}$ are identical or different and denote hydrogen or methyl, or $R^{14}$ and $R^{15}$ together form a cyclopentyl or cyclohexyl ring, or $R^{14}$ denotes hydrogen or methyl, and $R^{15}$ denotes cyclopropyl, cyclopentyl, cyclohexyl, phenyl or hydrogen; or denotes straight-chain or branched alkyl having up to six carbon atoms, where the alkyl is optionally substituted by methylthio, hydroxyl, mercapto, guanidyl, or by a group of the formula —$NR^{17}R^{18}$ or $R^{19}$—OC—, in which $R^{17}$ and $R^{18}$, independently of each other, denote hydrogen, straight-chain or branched alkyl having up to 6 carbon atoms, or phenyl, and $R^{19}$ denotes hydroxyl, benzyloxy, alkoxy having up to 6 carbon atoms, or the above-listed group —$NR^{17}R^{18}$, $R^{16}$ denotes straight-chain or branched alkyl having up to 6 carbon atoms which is optionally substituted by hydroxyl or by straight-chain or branched alkoxy having up to 4 carbon atoms; or denotes carboxyl, allyloxycarbonyl, straight-chain or branched alkoxycarbonyl having up to 6 carbon atoms, or benzyloxycarbonyl, or the alkyl is optionally substituted by cyclopropyl, cyclopentyl, cyclohexyl, or by optionally substituted phenyl wherein the substituents are hydroxyl, fluorine, chlorine, bromine, nitro, $C_1$-$C_8$-alkoxy, or by the group —$NR^{17}$—$R^{18}$, in which and $R^{17}$ and $R^{18}$ have the abovementioned meanings, or the alkyl group is optionally substituted by imidazolyl or indolyl, in which the corresponding —NH-functions are optionally protected by alkyl having up to 6 carbon atoms or by an amino protecting group, $R^8$ denotes a radical of the formula,

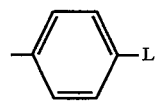

in which

L denotes phenyl or pyridyl, $R^9$ denotes hydrogen, straight-chain or branched alkyl having up to 4 carbon atoms, tert-butoxycarbonyl (Boc) or benzyloxycarbonyl (Z), $R^{10}$ denotes straight-chain or branched alkyl having up to 6 carbon atoms, phenoxy, phenyl, naphthyl, indolyl, quinolyl, quinoxalinyl, isoquinolyl, pyridyl, pyrazinyl, pyrimidyl, triazolyl or imidazolyl, wherein said phenoxy, phenyl, naphthyl and heterocyclic rings are optionally substituted identically or differently up to 3 times by nitro, carboxyl, cyano, hydroxyl, fluorine, chlorine, bromine, $C_1$-$C_4$ perhalogenoalkyl, straight-chain or branched $C_1$-$C_4$ alkyl, straight-chain or branched $C_1$-$C_4$ acyl, straight-chain or branched $C_1$-$C_4$ alkoxy or straight-chain or branched $C_1$-$C_4$ alkoxycarbonyl, and additionally said phenyl group is optionally substituted by optionally substituted pyridyl or optionally substituted triazolyl, wherein the substituent is phenyl, or $R^{10}$ denotes a radical of the formula

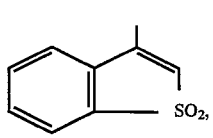
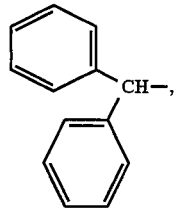
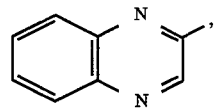
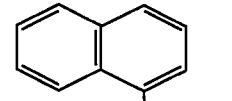
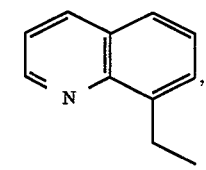
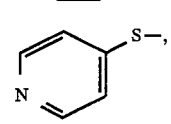

-continued

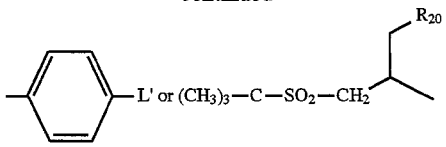

in which
L' has the abovementioned meaning of L and is identical to or different from the latter,
$R^{20}$ denotes phenyl or naphthyl,
c denotes a number 0, 1, 2 or 3,
d denotes a number 0, 1 or 2,
$R^{11}$ has the abovementioned meaning of $R^{10}$ and is identical to or different from the latter,
$R^{12}$ denotes methyl or phenyl which is optionally substituted identically or differently by methyl or methoxy or denotes a radical of the formula

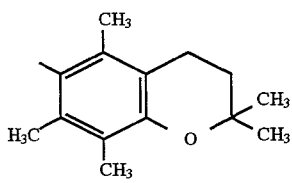

$R^2$, $R^3$, $R^5$ and $R^6$ are identical or different and denote Boc, hydrogen, methyl, ethyl, benzyloxycarbonyl or tert-butyl,
$R^4$ represents nitro, benzyloxycarbonyl or tert-butoxycarbonyl, or represents a radical of the formula $-SO_2-R^{21}$,
in which
$R^{21}$ has the abovementioned meaning of $R^{12}$ and is identical to or different from the latter,
$R^7$ represents formyl or carboxyl, or represents straight-chain or branched alkoxycarbonyl having up to 6 carbon atoms, or represents a radical of the formula $-CH_2-OR^{22}$ or $-CH(OR^{23})_2$,
in which
$R^{22}$ and $R^{23}$ are identical or different and denote hydrogen, straight-chain or branched alkyl having up to 4 carbon atoms, acetyl or benzyl,
or a salt thereof,
with the proviso that if a represents the number 2, b represents the number 1 and $R^5$ represents hydrogen, $R^1$ may not denote the radical of the formula $R^8-NH-CO$.

3. A compound according to claim 1, in which
a represents a number 2 or 3,
b represents a number 0 or 1,
$R^1$ represents hydrogen, or represents a radical of the formula $R^8-NR^9-CO-$, $R^{10}-(CH_2)_c-CO-$, $R^{11}-(CH_2)_d-O-CO$, or represents a radical of the formula $-SO_2R^{12}$,
in which
$R^8$ denotes cyclopentyl, or cyclohexyl; or denotes optionally substituted straight-chain or branched alkyl having up to 14 carbon atoms wherein the substituents are hydroxyl, methoxy, fluorine, trifluoromethyl, trifluoromethoxy, cyclohexyl, phenyl, or alkyl which is optionally substituted by a group of the formula $-CO_2-R^{13}$, in which
$R^{13}$ denotes hydrogen, or straight-chain or branched alkyl or alkenyl having in each case up to 4 carbon atoms, or benzyl,
or
$R^8$ denotes phenyl which is optionally substituteed identically or different up to 2 times by carboxyl, fluorine, hydroxyl, cyano, trifluoromethyl or amino, or straight-cahin or branched $C_1-C_4$-acyl, straight-chain or branched $C_1-C_4$ alkoxy, vinyl-$C_1-C_4$-alkoxycarbonyl or straight-chain or branched alkoxycarbonyl, or denotes an amino acid radical of the formula,

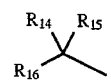

in which
$R^{14}$ and $R^{15}$ are identical or different and denote hydrogen or methyl, or
$R^{14}$ and $R^{15}$ together form a cyclopentyl or cyclohexyl ring,
or
$R^{14}$ denotes hydrogen or methyl,
and
$R^{15}$ denotes cyclopropyl, cyclopentyl, cyclohexyl, phenyl or hydrogen; or denotes straight-chain or branched alkyl having up to 6 carbon atoms, where the alkyl is optionally substituted by methylthio, hydroxyl, mercapto, guanidyl, or by a group of the formula $-NR^{17}R^{18}$ or $R^{19}-OC-$,
in which
$R^{17}$ and $R^{18}$, independently of each other, denote hydrogen, straight-chain or branched alkyl having up to 6 carbon atoms, or phenyl,
and
$R^{19}$ denotes hydroxyl, benzyloxy, alkoxy having up to 4 carbon atoms, or the above-listed group $-NR^{17}R^{18}$,
$R^{16}$ denotes straight-chain or branched alkyl having up to 4 carbon atoms which is optionally substituted by hydroxyl or straight-chain or branched alkoxy having up to 3 carbon atoms, or denotes carboxyl, allyloxycarbonyl, straight-chain or branched alkoxycarbonyl having up to 4 carbon atoms, or benzyloxycarbonyl,
or the alkyl is optionally substituted by cyclopropyl, cyclopentyl, cyclohexyl, or by optionally substituted phenyl wherein the substituents are fluorine, chlorine, bromine, nitro $C_1-C_6$ alkoxy or by the group $-NR^{17}R^{18}$,
in which
$R^{17}$ and $R^{18}$ have the abovementioned meanings,
or the alkyl is optionally substituted by imidazolyl or indolyl in which the corresponding $-NH-$ functions are optionally protected by alkyl having up to 4 carbon atoms, tert-butoxycarbonyl or benzyloxycarbonyl, $R^8$ denotes a radical of the formula,

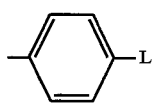

in which

L denotes phenyl or pyridyl, $R^9$ denotes hydrogen, methyl, ethyl or tert-butyl, $R^{10}$ denotes straight-chain or branched alkyl having up to 6 carbon atoms, phenoxy, phenyl, naphthyl, indolyl, quinolyl, quinoxalinyl, isoquinolyl, pyridyl, pyrazinyl, pyrimidyl, triazolyl or imidazolyl, wherein said phenoxy, phenyl, naphthyl and heterocyclic rings are optionally subtituted identically or differently up to 3 times by nitro, carboxyl, cyano, hyroxyl, fluorine, chlorine, bromine, $C_1$-$C_4$ perhalogenoalkyl or by straight-chain or branched $C_1$-$C_4$ alkyl, straight-chain or branched $C_1$-$C_4$ acyl, straight-chain or branched $C_1$-$C_4$ alkoxy, or straight-chain or branched $C_1$-$C_4$ alkoxycarbonyl and additionally said phenyl group is optionally substituted by optionally substituent pyridyl or optionally substituted triazolyl, wherein the substituents is phenyl, or $R^{10}$ denotes a radical of the formula

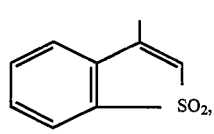
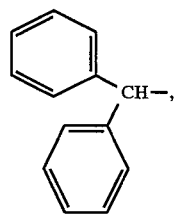
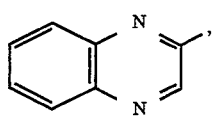
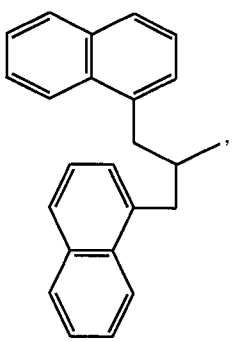
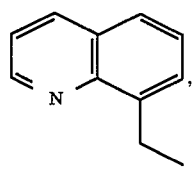
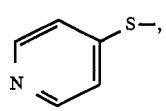
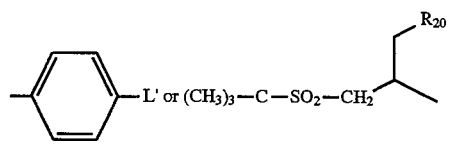

in which

L' has the abovementioned meaning of L and is identical to or different from the latter, $R^{20}$ denotes phenyl or naphthyl, c denotes a number 0, 1, 2 or 3, d denotes a number 0, 1 or 2, $R^{11}$ has the abovementioned meaning of $R^{10}$ and is identical to or different from the latter, $R^{12}$ denotes methyl or phenyl which optionally substituted identically or differently up to 4 times by methyl or methoxy, or denotes a radical of the formula

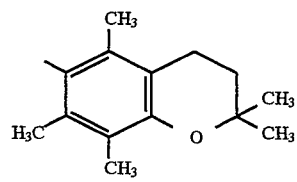

$R^2$, $R^3$, $R^5$ and $R^6$ are identical or different and denote Boc, hydrogen, methyl, ethyl, benzyloxycarbonyl or tert-butyl, $R^4$ represents nitro, benzyloxycarbonyl or tert-butoxycarbonyl, or represents a radical of the formula —$SO_2R^{21}$, in which $R^{21}$ has the abovementioned meaning of $R^{12}$ and is identical to or different from the latter, $R^7$ represents formyl or carboxyl, or represents straight-chain or branched alkoxycarbonyl having up to 4 carbon atoms, or represents a radical of the formula —$CH_2$—$OR^{22}$ or —$CH(OR^{23})_2$, in which $R^{22}$ and $R^{23}$ are identical or different and denote hydrogen, straight-chain or branched alkyl having up to 3 carbon atoms, or benzyl, or a salt thereof, with the proviso that if a represents the number 2, b represents the number 1 and $R^5$ represents hydrogen, $R^1$ may not represent the radical of the formula $R^8$—NH—CO—.

4. A compound according to claim 1, wherein a is 2, b is 1, $R^1$ is $R^{10}$—$(CH_2)_c$—CO— or $R^{11}$—$(CH_2)_d$—O—CO— wherein $R^{10}$ and $R^{11}$ are optionally substituted quinolyl, quinoxalinyl or phenyl;

$R^4$ is $SO_2R^{21}$ wherein $R^{21}$ is optionally substituted phenyl and the substituents are methyl or methoxy; and $R^7$ is formyl.

5. A compound according to claim 4, wherein $R^1$ is $R^{10}$—$(CH_2)_c$—CO—.

6. The compound according to claim 1, which has the formula

7. The compound according to claim 1, which has the formula
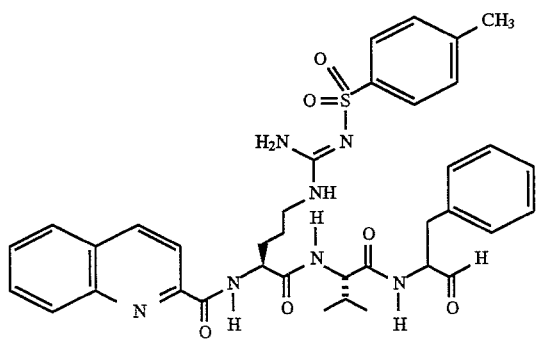
8. A pharmaceutical composition which comprises a pharmaceutically effective amount of a compound according to claim 1 and a diluent.
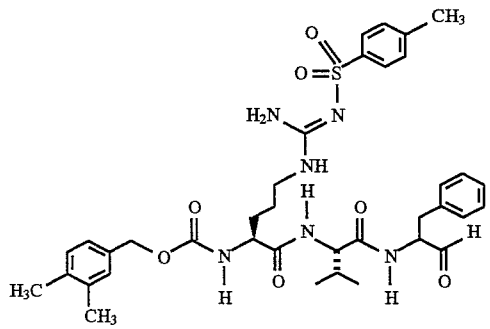
* * * * *

UNITED STATES PATENT AND TRADEMARK OFFICE
CERTIFICATE OF CORRECTION

PATENT NO. : 5,633,231
DATED      : May 27, 1997
INVENTOR(S): Habich, et al.

It is certified that error appears in the above-indentified patent and that said Letters Patent is hereby corrected as shown below:

Title Page        Line 2 after " [45] Date of Patent: " insert -- * --

Title Page        Under " [73] " insert -- [*] Notice : The term of this patent shall not extend beyond the expiration date of Pat. No. 5,492,896 --

Col. 63, line 66  Delete " and "

Signed and Sealed this

Twelfth Day of May, 1998

*Attest:*

*Attesting Officer*

BRUCE LEHMAN

*Commissioner of Patents and Trademarks*